(12) United States Patent
Bykowski et al.

(10) Patent No.: US 11,156,378 B2
(45) Date of Patent: Oct. 26, 2021

(54) PERSONAL HEALTH MONITORING USING SMART HOME DEVICES

(71) Applicant: Johnson Controls Technology Company, Auburn Hills, MI (US)

(72) Inventors: Ryan J. Bykowski, South Milwaukee, WI (US); Scott Ambelang, Milwaukee, WI (US); Daniel R. Gottschalk, Racine, WI (US); Eric Mackey, Milwaukee, WI (US)

(73) Assignee: Johnson Controls Tyco IP Holdings LLP, Milwaukee, WI (US)

( * ) Notice: Subject to any disclaimer, the term of this patent is extended or adjusted under 35 U.S.C. 154(b) by 0 days.

(21) Appl. No.: 16/749,900

(22) Filed: Jan. 22, 2020

(65) Prior Publication Data

US 2021/0222903 A1    Jul. 22, 2021

(51) Int. Cl.
| | | |
|---|---|---|
| *A61B 5/145* | (2006.01) |
| *F24F 11/52* | (2018.01) |
| *G01N 33/00* | (2006.01) |
| *G01N 33/497* | (2006.01) |
| *F24F 11/64* | (2018.01) |
| *F24F 11/30* | (2018.01) |
| *F24F 110/65* | (2018.01) |
| *F24F 120/12* | (2018.01) |
| *F24F 110/66* | (2018.01) |

(52) U.S. Cl.
CPC .............. *F24F 11/52* (2018.01); *A61B 5/145* (2013.01); *F24F 11/30* (2018.01); *F24F 11/64* (2018.01); *G01N 33/0047* (2013.01); *G01N 33/4972* (2013.01); *F24F 2110/65* (2018.01); *F24F 2110/66* (2018.01); *F24F 2120/12* (2018.01)

(58) Field of Classification Search
CPC ....... A61B 2560/0242; A61B 5/14551; H04W 4/38
See application file for complete search history.

(56) References Cited

U.S. PATENT DOCUMENTS

| | | | |
|---|---|---|---|
| 2015/0194039 A1* | 7/2015 | Martin | H04W 72/0453 340/632 |
| 2015/0372832 A1* | 12/2015 | Kortz | H04L 12/2818 700/278 |
| 2018/0168464 A1* | 6/2018 | Barnett, Jr. | A61B 5/6826 |

* cited by examiner

*Primary Examiner* — Benyam Haile
(74) *Attorney, Agent, or Firm* — Foley & Lardner LLP

(57) ABSTRACT

A sensor unit includes an air quality sensor configured to generate air quality data that includes a value for volatile organic compounds. The sensor unit is configured to determine a first health metric indicative of a condition within a space in which the sensor unit is located based on the value in a first mode of operation, to determine a second health metric indicative of a person's health based on the value in a second mode of operation, and to generate a notification indicating at least one of the first health metric or the second health metric.

20 Claims, 10 Drawing Sheets

PERSONAL HEALTH MONITORING USING SMART HOME DEVICES

BACKGROUND

The present disclosure relates generally to smart home devices. More specifically, the present disclosure relates to systems and methods for determining health metrics using a smart home device.

A smart home system may include a variety of different smart home devices and equipment located within a building. The smart home devices may be configured to monitor and/or control environmental conditions within the building. In some implementations, smart home devices include space controllers, which may be used to generate control decisions and operate, based on the control decisions, at least one piece of building equipment. For example, the smart home device may include a thermostat used to monitor and control the temperature within the building based on sensor data from a temperature sensor. These smart home devices may also include other onboard sensors to monitor different environmental conditions besides temperature.

SUMMARY OF THE INVENTION

One embodiment of the present disclosure is a sensor unit. The sensor unit includes an air quality sensor configured to generate air quality data that includes a value for volatile organic compounds. The sensor unit is configured to determine a first health metric indicative of a condition within a space in which the sensor unit is located based on the value in a first mode of operation, to determine a second health metric indicative of a person's health based on the value in a second mode of operation, and to generate a notification indicating at least one of the first health metric or the second health metric.

In some embodiments, the sensor unit is part of a thermostat that includes a temperature sensor configured to measure a temperature. The thermostat may further include a user interface configured to receive input from the user and to operate a controlled device based on the input. The input may include a temperature preference.

In some embodiments, in the first mode of operation, the sensor unit is configured to continuously generate air quality data while the sensor unit is powered on.

In some embodiments, in the second mode of operation, the sensor unit is configured to generate air quality data from air flowing over the air quality sensor over a predefined time interval. For example, the second health metric may be a blood alcohol content and the notification may be indicative of whether the blood alcohol content exceeds a legal blood alcohol limit.

In some embodiments, the sensor unit further includes a proximity sensor. The sensor unit may be configured to switch to the second mode based on sensor data from the proximity sensor indicating a person is within a predefined range of the sensor unit.

In some embodiments, the sensor unit further includes a user interface configured to display the notification and receive user input. The sensor unit may be configured to operate in one of the first mode and the second mode based on the user input.

In some embodiments, the sensor unit is configured to store air quality data from the air quality sensor over a predefined time interval, to determine a third health metric based on the air quality data over the predefined time interval, and to generate a notification indicating the third health metric.

Another embodiment of the present disclosure is a space controller. The space controller is disposed within a building and is configured to operate a controlled device. The space controller includes a user interface, an air quality sensor, and a processing circuit. The user interface is configured to present information to a user. The air quality sensor is configured to generate air quality data including a value for volatile organic compounds. The processing circuit is configured to receive air quality data from the air quality sensor, to determine a first health metric indicative of a condition within a space in which the sensor unit is located based on the value in a first mode of operation, to determine a second health metric indicative of a person's health based on the value in a second mode of operation, to generate a notification indicating at least one of the first health metric or the second health metric, and to cause the user interface to display the notification.

In some embodiments, the space controller is a thermostat including a temperature sensor that is configured to measure a temperature. The user interface may be further configured to receive input from the user and to operation the controlled device based on the input. The input may be a temperature preference.

In some embodiments, in the first mode of operation, the processing circuit is configured to continuously receive air quality data from the air quality sensor while the space controller is powered on.

In some embodiments, in the second mode of operation, the processing circuit is configured to receive air quality data from the air quality sensor over a predetermined time interval.

In some embodiments, the space controller further includes a memory configured to store air quality data from the air quality sensor over a predefined time interval. The processing circuit may be configured to determine a third heath metric based on the air quality data over the predefined time interval. In some embodiments, the processing circuit is configured to cause the user interface to display the third health metric.

Another embodiment of the present disclosure is a method. The method includes receiving, from an air quality sensor within a building, air quality data including a value for volatile organic compounds. The method also includes determining a first health metric indicative of a condition within a space in which the air quality sensor is located based on the value in a first mode of operation, and determining a second health metric indicative of a person's health based on the value in a second mode of operation. The method additionally includes generating a notification indicating at least one of the first health metric or the second health metric. The method further includes operating a controlled device based on a determination that at least one of the first health metric or the second health metric exceeds a threshold value.

In some embodiments, the controller device is operated to prevent a user from at least one of accessing a space within a building or operating the controlled device.

In some embodiments, the method further includes receiving, in the second mode of operation, air quality data from the air quality sensor over a predefined time interval.

In some embodiments, the controlled device is one of a door lock, a security system, a vehicle, or a garage door.

BRIEF DESCRIPTION OF THE DRAWINGS

Various objects, aspects, features, and advantages of the disclosure will become more apparent and better understood by referring to the detailed description taken in conjunction with the accompanying drawings, in which like reference characters identify corresponding elements throughout. In the drawings, like reference numbers generally indicate identical, functionally similar, and/or structurally similar elements.

DETAILED DESCRIPTION

Overview

Figure 1:
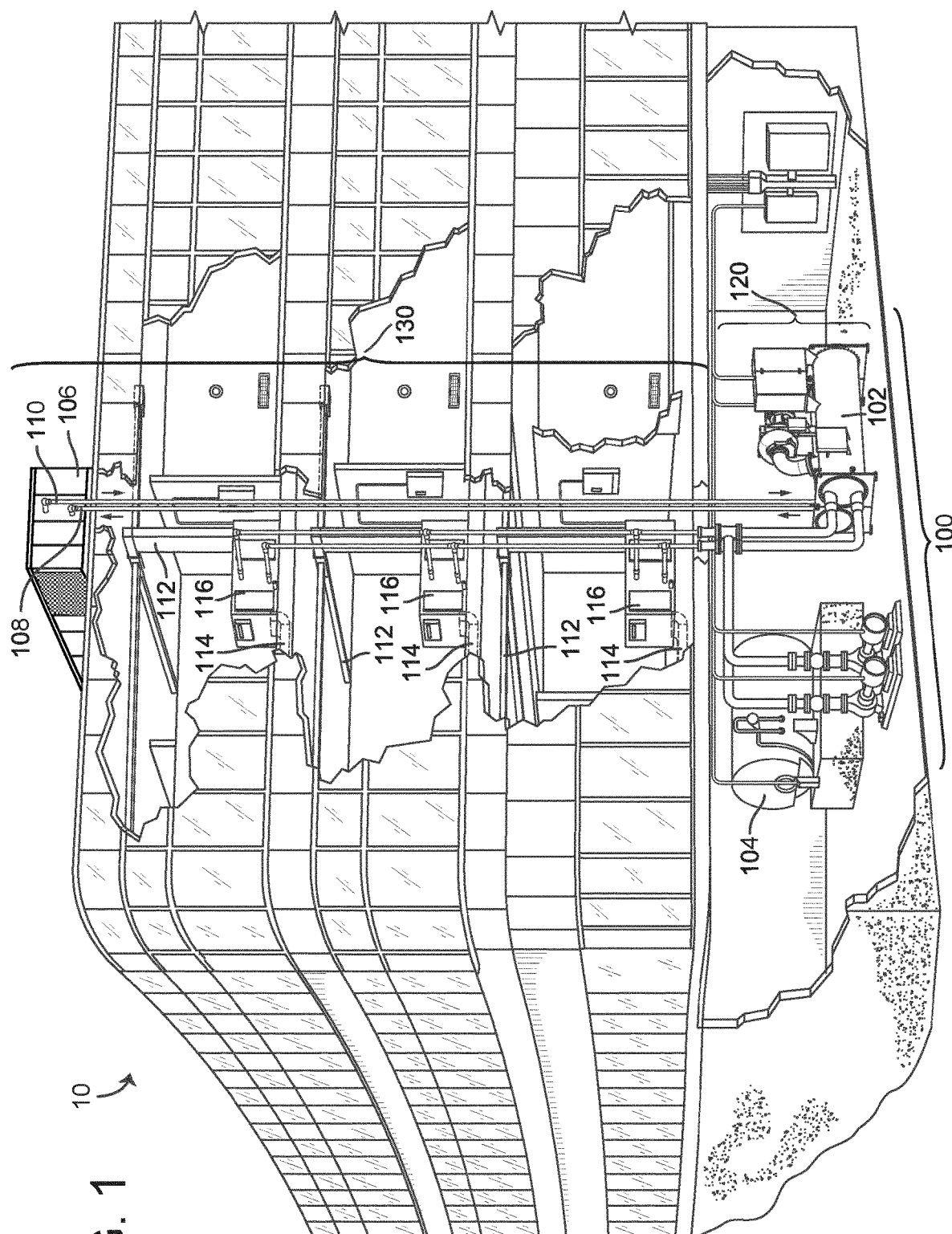
FIG. 1 is a drawing of a building equipped with a building management system, according to an exemplary embodiment.

Referring generally to the figures, a personal health monitoring system for a building is shown, according to various exemplary embodiments. The system includes a space controller located within the building. The space controller may include an air quality sensor configured to generate air quality data for a room or space within the building. The air quality data may be indicative of an amount and/or value of carbon monoxide (CO), carbon dioxide (CO2), and/or volatile organic compounds (VOC) present within the room or space. The value for VOCs may include, for example, an amount of ethanol or ethanol content within the room or space. According to various exemplary embodiments, the space controller is configured to determine a health value based on the air quality data. For example, the space controller may be configured to determine an average amount of CO, CO2, VOCs, etc. within the room or space. Additionally, the space controller may be configured to determine a health value indicative of a person's health by sampling air from a micro-environment generated by the person in close-range of the space controller. For example, the space controller may be configured to determine a blood alcohol content (BAC) based on the value for VOCs that is measured within the room or space. More particularly, the space controller may be configured to receive air that is exhaled from an occupant of the room or space, and to determine an estimated BAC from the value for VOCs that is measured from the air. The space controller may be configured to generate a notification indicating the BAC and to display the notification on a user interface of the space controller.

In some embodiments, the personal health monitoring system additionally includes a sensor unit disposed in the building remotely from the space controller. For example, the sensor unit may be located in a different room from the space controller or in a different area within the same room where the space controller is located. The sensor unit may be communicably coupled to the space controller. The sensor unit may include an air quality sensor. In some embodiments, the sensor unit may be communicably coupled to a space controller that does not include its own air quality sensor. In other embodiments, both the sensor unit and the space controller include an air quality sensor. The sensor unit may be configured to determine a BAC based on the value for VOCs (e.g., an ethanol content of air, etc.) measured by the sensor unit. Additionally, the sensor unit may be configured to generate a notification indicating the BAC. In some embodiments, the sensor unit is configured to transmit the notification to the space controller.

In some embodiments, the space controller is configured to take remedial action based on one, or a combination of, the BAC and the notification. For example, the space controller may be configured to operate a controlled device based on a determination that the BAC exceeds a threshold value (e.g., a legal BAC limit or another threshold value). More particularly, the space controller may be configured to operate the controlled device based on the BAC to prevent a user from at least one of accessing a space within the building or operating the controlled device. The controlled device may be a door lock of a door between rooms (e.g., lab space, workshop, etc.) within a building, a security system, a vehicle (e.g., a car, truck, a forklift, etc.), or a garage door or vehicle access door. Among other benefits, selectively restricting access to different rooms and/or user operated equipment reduces the risk of harm or injury associated with operating the equipment while intoxicated. Restricting access based on BAC may be particularly beneficial in industrial environments (e.g., job sites, etc.) where liability issues may result from a laborer or technician performing work while intoxicated.

In some embodiments, the space controller is configured to transmit one, or a combination of the notification and the BAC to a remote computing device (e.g., a remote server, a cloud computing device, etc.). Data relating to BAC and/or other monitored conditions within the room or space may be accessed through a software application (e.g., an app on a mobile phone, a laptop computer, etc.). The data may be used to selectively restrict a user's from accessing certain services. For example, the data may be used to prevent a user from accessing financial information or from communicating with select individuals. In some embodiments, the data may be accessed by law enforcement officials for monitoring individuals on parole.

In some embodiments, the data relating to BAC or other health values/metrics may be used to assess the overall health and wellness of a user. For example, the space controller may include memory that is configured to store air quality data over a predefined time interval. The space controller and/or the remote computing device may use the air quality data to determine historical trends for BAC and/or other health values. In some embodiments, the historical trends may be analyzed or otherwise used to identify early signs of a serious problem (e.g., excessive drinking, increased risk of stroke, etc.). The details of the foregoing depiction will be more fully explained by reference to the various individual embodiments.

Building Management System and HVAC System

Figure 2:
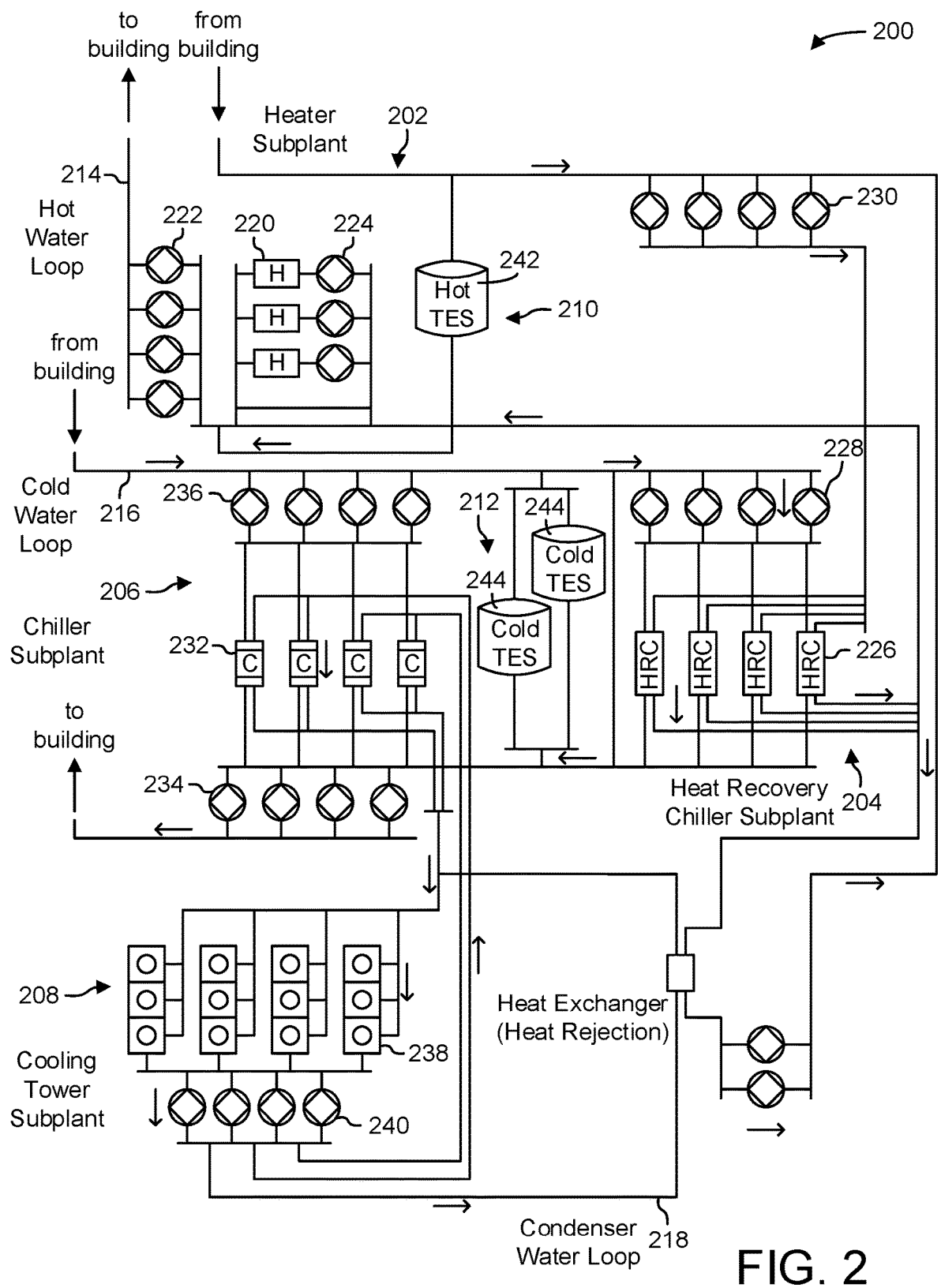
FIG. 2 is a block diagram of a waterside system that may be used in conjunction with the building of FIG. 1, according to an exemplary embodiment.
Figure 3:
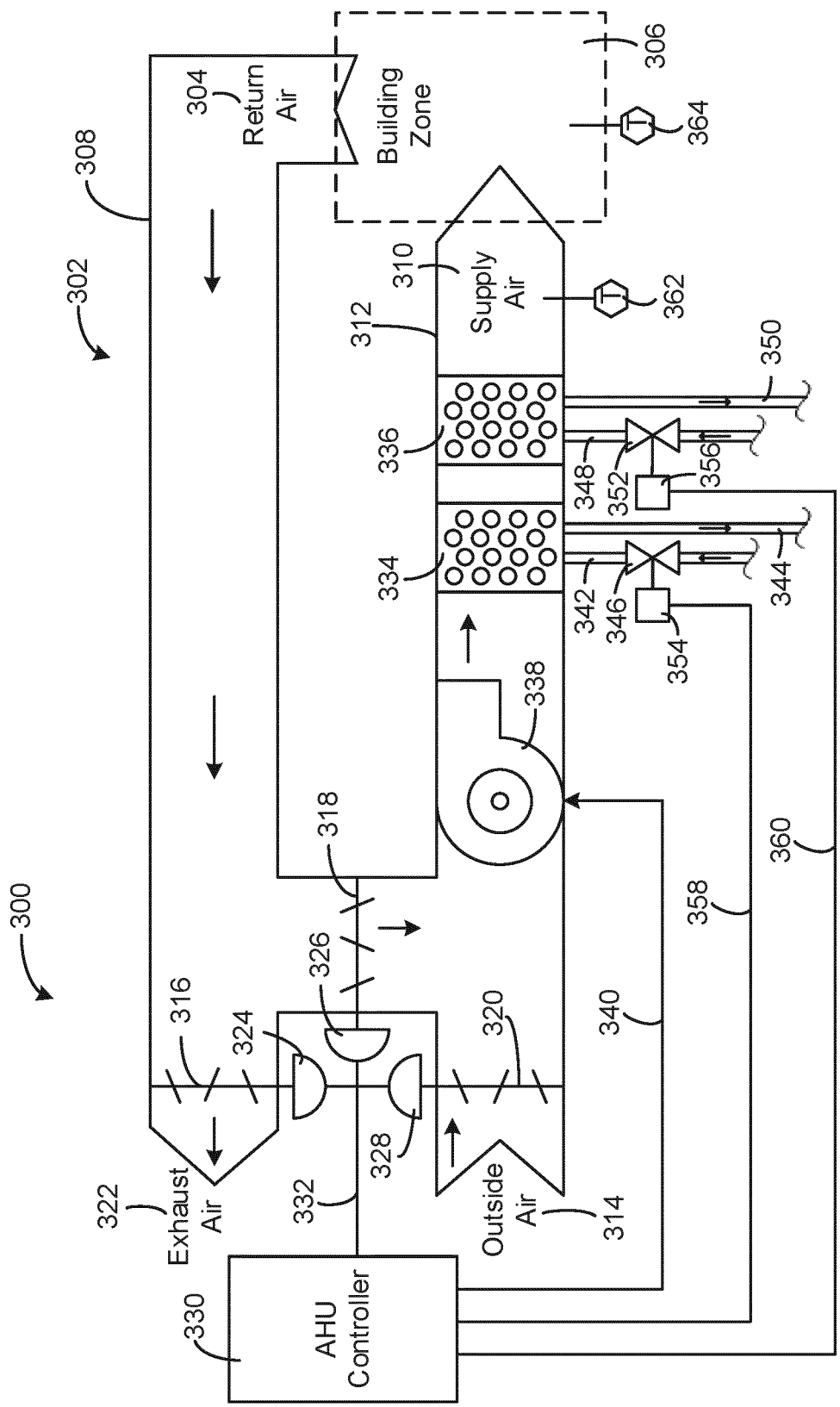
FIG. 3 is a block diagram of an airside system that may be used in conjunction with the building of FIG. 1, according to an exemplary embodiment.

Referring now to FIGS. 1-3, an exemplary building management system (BMS) and HVAC system in which the systems and methods of the present invention can be implemented are shown, according to an exemplary embodiment. Referring particularly to FIG. 1, a perspective view of a building 10 is shown. Building 10 is served by a BMS. A BMS is, in general, a system of devices configured to control, monitor, and manage controlled devices and equipment in or around a building or building area. A BMS can include, for example, a HVAC system, a security system, a lighting system, a fire alerting system, any other system that is capable of managing building functions or devices, or any combination thereof. Controlled devices that can be managed or operated by the BMS may include electronically actuated equipment (e.g., door locks, garage doors, etc.) and/or remotely operated electronic equipment such as a vehicle (e.g., remote car doors, ignition system, etc.).

The BMS that serves building 10 includes an HVAC system 100. HVAC system 100 can include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 can provide a heated or chilled fluid to an air handling unit of airside system 130. Airside system 130 can use the heated or chilled fluid to heat or cool an airflow provided to building 10. An exemplary waterside system and airside system which can be used in HVAC system 100 are described in greater detail with reference to FIGS. 2-3.

HVAC system 100 is shown to include a chiller 102, a boiler 104, and a rooftop air handling unit (AHU) 106. Waterside system 120 can use boiler 104 and chiller 102 to heat or cool a working fluid (e.g., water, glycol, etc.) and can circulate the working fluid to AHU 106. In various embodiments, the HVAC devices of waterside system 120 can be located in or around building 10 (as shown in FIG. 1) or at an offsite location such as a central plant (e.g., a chiller plant, a steam plant, a heat plant, etc.). The working fluid can be heated in boiler 104 or cooled in chiller 102, depending on whether heating or cooling is required in building 10. Boiler 104 can add heat to the circulated fluid, for example, by burning a combustible material (e.g., natural gas) or using an electric heating element. Chiller 102 can place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 can be transported to AHU 106 via piping 108.

AHU 106 can place the working fluid in a heat exchange relationship with an airflow passing through AHU 106 (e.g., via one or more stages of cooling coils and/or heating coils). The airflow can be, for example, outside air, return air from within building 10, or a combination of both. AHU 106 can transfer heat between the airflow and the working fluid to provide heating or cooling for the airflow. For example, AHU 106 can include one or more fans or blowers configured to pass the airflow over or through a heat exchanger containing the working fluid. The working fluid can then return to chiller 102 or boiler 104 via piping 110.

Airside system 130 can deliver the airflow supplied by AHU 106 (i.e., the supply airflow) to building 10 via air supply ducts 112 and can provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 can include dampers or other flow control elements that can be operated to control an amount of the supply airflow provided to individual zones of building 10. In other embodiments, airside system 130 delivers the supply airflow into one or more zones of building 10 (e.g., via supply ducts 112) without using intermediate VAV units 116 or other flow control elements. AHU 106 can include various sensors (e.g., temperature sensors, pressure sensors, etc.) configured to measure attributes of the supply airflow. AHU 106 can receive input from sensors located within AHU 106 and/or within the building zone and can adjust the flow rate, temperature, or other attributes of the supply airflow through AHU 106 to achieve set-point conditions for the building zone.

Referring now to FIG. 2, a block diagram of a waterside system 200 is shown, according to an exemplary embodiment. In various embodiments, waterside system 200 can supplement or replace waterside system 120 in HVAC system 100 or can be implemented separate from HVAC system 100. When implemented in HVAC system 100, waterside system 200 can include a subset of the HVAC devices in HVAC system 100 (e.g., boiler 104, chiller 102, pumps, valves, etc.) and can operate to supply a heated or chilled fluid to AHU 106. The HVAC devices of waterside system 200 can be located within building 10 (e.g., as components of waterside system 120) or at an offsite location such as a central plant.

In FIG. 2, waterside system 200 is shown as a central plant having a plurality of subplants 202-212. Subplants 202-212 are shown to include a heater subplant 202, a heat recovery chiller subplant 204, a chiller subplant 206, a cooling tower subplant 208, a hot thermal energy storage (TES) subplant 210, and a cold thermal energy storage (TES) subplant 212. Subplants 202-212 consume resources (e.g., water, natural gas, electricity, etc.) from utilities to serve the thermal energy loads (e.g., hot water, cold water, heating, cooling, etc.) of a building or campus. For example, heater subplant 202 can be configured to heat water in a hot water loop 214 that circulates the hot water between heater subplant 202 and building 10. Chiller subplant 206 can be configured to chill water in a cold water loop 216 that circulates the cold water between chiller subplant 206 building 10. Heat recovery chiller subplant 204 can be configured to transfer heat from cold water loop 216 to hot water loop 214 to provide additional heating for the hot water and additional cooling for the cold water. Condenser water loop 218 can absorb heat from the cold water in chiller subplant 206 and reject the absorbed heat in cooling tower subplant 208 or transfer the absorbed heat to hot water loop 214. Hot TES subplant 210 and cold TES subplant 212 can store hot and cold thermal energy, respectively, for subsequent use.

Hot water loop 214 and cold water loop 216 can deliver the heated and/or chilled water to air handlers located on the rooftop of building 10 (e.g., AHU 106) or to individual floors or zones of building 10 (e.g., VAV units 116). The air handlers push air past heat exchangers (e.g., heating coils or cooling coils) through which the water flows to provide heating or cooling for the air. The heated or cooled air can be delivered to individual zones of building 10 to serve the thermal energy loads of building 10. The water then returns to subplants 202-212 to receive further heating or cooling.

Although subplants 202-212 are shown and described as heating and cooling water for circulation to a building, it is understood that any other type of working fluid (e.g., glycol, $CO_2$, etc.) can be used in place of or in addition to water to serve the thermal energy loads. In other embodiments, subplants 202-212 can provide heating and/or cooling directly to the building or campus without requiring an intermediate heat transfer fluid. These and other variations to waterside system 200 are within the teachings of the present invention.

Each of subplants 202-212 can include a variety of equipment configured to facilitate the functions of the subplant. For example, heater subplant 202 is shown to include a plurality of heating elements 220 (e.g., boilers, electric heaters, etc.) configured to add heat to the hot water in hot water loop 214. Heater subplant 202 is also shown to include several pumps 222 and 224 configured to circulate the hot water in hot water loop 214 and to control the flow rate of the hot water through individual heating elements 220. Chiller subplant 206 is shown to include a plurality of chillers 232 configured to remove heat from the cold water in cold water loop 216. Chiller subplant 206 is also shown to include several pumps 234 and 236 configured to circulate the cold water in cold water loop 216 and to control the flow rate of the cold water through individual chillers 232.

Heat recovery chiller subplant 204 is shown to include a plurality of heat recovery heat exchangers 226 (e.g., refrigeration circuits) configured to transfer heat from cold water loop 216 to hot water loop 214. Heat recovery chiller subplant 204 is also shown to include several pumps 228 and 230 configured to circulate the hot water and/or cold water through heat recovery heat exchangers 226 and to control the flow rate of the water through individual heat recovery heat exchangers 226. Cooling tower subplant 208 is shown to include a plurality of cooling towers 238 configured to remove heat from the condenser water in condenser water loop 218. Cooling tower subplant 208 is also shown to include several pumps 240 configured to circulate the condenser water in condenser water loop 218 and to control the flow rate of the condenser water through individual cooling towers 238.

Hot TES subplant 210 is shown to include a hot TES tank 242 configured to store the hot water for later use. Hot TES subplant 210 can also include one or more pumps or valves configured to control the flow rate of the hot water into or out of hot TES tank 242. Cold TES subplant 212 is shown to include cold TES tanks 244 configured to store the cold water for later use. Cold TES subplant 212 can also include one or more pumps or valves configured to control the flow rate of the cold water into or out of cold TES tanks 244.

In some embodiments, one or more of the pumps in waterside system 200 (e.g., pumps 222, 224, 228, 230, 234, 236, and/or 240) or pipelines in waterside system 200 include an isolation valve associated therewith. Isolation valves can be integrated with the pumps or positioned upstream or downstream of the pumps to control the fluid flows in waterside system 200. In various embodiments, waterside system 200 can include more, fewer, or different types of devices and/or subplants based on the particular configuration of waterside system 200 and the types of loads served by waterside system 200.

Referring now to FIG. 3, a block diagram of an airside system 300 is shown, according to an exemplary embodiment. In various embodiments, airside system 300 can supplement or replace airside system 130 in HVAC system 100 or can be implemented separate from HVAC system 100. When implemented in HVAC system 100, airside system 300 can include a subset of the HVAC devices in HVAC system 100 (e.g., AHU 106, VAV units 116, ducts 112-114, fans, dampers, etc.) and can be located in or around building 10. Airside system 300 can operate to heat or cool an airflow provided to building 10 using a heated or chilled fluid provided by waterside system 200.

In FIG. 3, airside system 300 is shown to include an economizer-type air handling unit (AHU) 302. Economizer-type AHUs vary the amount of outside air and return air used by the air handling unit for heating or cooling. For example, AHU 302 can receive return air 304 from building zone 306 via return air duct 308 and can deliver supply air 310 to building zone 306 via supply air duct 312. In some embodiments, AHU 302 is a rooftop unit located on the roof of building 10 (e.g., AHU 106 as shown in FIG. 1) or otherwise positioned to receive both return air 304 and outside air 314. AHU 302 can be configured to operate exhaust air damper 316, mixing damper 318, and outside air damper 320 to control an amount of outside air 314 and return air 304 that combine to form supply air 310. Any return air 304 that does not pass through mixing damper 318 can be exhausted from AHU 302 through exhaust air damper 316 as exhaust air 322.

Each of dampers 316-320 can be operated by an actuator. For example, exhaust air damper 316 can be operated by actuator 324, mixing damper 318 can be operated by actuator 326, and outside air damper 320 can be operated by actuator 328. Actuators 324-328 can communicate with an AHU controller 330 via a communications link 332. Actuators 324-328 can receive control signals from AHU controller 330 and can provide feedback signals to AHU controller 330. Feedback signals can include, for example, an indication of a current actuator or damper position, an amount of torque or force exerted by the actuator, diagnostic information (e.g., results of diagnostic tests performed by actuators 324-328), status information, commissioning information, configuration settings, calibration data, and/or other types of information or data that can be collected, stored, or used by actuators 324-328. AHU controller 330 can be an economizer controller configured to use one or more control algorithms (e.g., state-based algorithms, extremum seeking control (ESC) algorithms, proportional-integral (PI) control algorithms, proportional-integral-derivative (PID) control algorithms, model predictive control (MPC) algorithms, feedback control algorithms, etc.) to control actuators 324-328.

Still referring to FIG. 3, AHU 302 is shown to include a cooling coil 334, a heating coil 336, and a fan 338 positioned within supply air duct 312. Fan 338 can be configured to force supply air 310 through cooling coil 334 and/or heating coil 336 and provide supply air 310 to building zone 306. AHU controller 330 can communicate with fan 338 via communications link 340 to control a flow rate of supply air 310. In some embodiments, AHU controller 330 controls an amount of heating or cooling applied to supply air 310 by modulating a speed of fan 338.

Cooling coil 334 can receive a chilled fluid from waterside system 200 (e.g., from cold water loop 216) via piping 342 and can return the chilled fluid to waterside system 200 via piping 344. Valve 346 can be positioned along piping 342 or piping 344 to control a flow rate of the chilled fluid through cooling coil 334. In some embodiments, cooling coil 334 includes multiple stages of cooling coils that can be independently activated and deactivated (e.g., by AHU controller 330, by BMS controller, etc.) to modulate an amount of cooling applied to supply air 310.

Heating coil 336 can receive a heated fluid from waterside system 200 (e.g., from hot water loop 214) via piping 348 and can return the heated fluid to waterside system 200 via piping 350. Valve 352 can be positioned along piping 348 or piping 350 to control a flow rate of the heated fluid through heating coil 336. In some embodiments, heating coil 336 includes multiple stages of heating coils that can be independently activated and deactivated (e.g., by AHU controller 330, by BMS controller, etc.) to modulate an amount of heating applied to supply air 310.

Each of valves 346 and 352 can be controlled by an actuator. For example, valve 346 can be controlled by actuator 354 and valve 352 can be controlled by actuator 356. Actuators 354-356 can communicate with AHU controller 330 via communications links 358-360. Actuators 354-356 can receive control signals from AHU controller 330 and can provide feedback signals to controller 330. In some embodiments, AHU controller 330 receives a measurement of the supply air temperature from a temperature sensor 362 positioned in supply air duct 312 (e.g., downstream of cooling coil 334 and/or heating coil 336). AHU controller 330 can also receive a measurement of the temperature of building zone 306 from a temperature sensor 364 located in building zone 306.

In some embodiments, AHU controller 330 operates valves 346 and 352 via actuators 354-356 to modulate an amount of heating or cooling provided to supply air 310 (e.g., to achieve a set-point temperature for supply air 310 or to maintain the temperature of supply air 310 within a set-point temperature range). The positions of valves 346 and 352 affect the amount of heating or cooling provided to supply air 310 by cooling coil 334 or heating coil 336 and may correlate with the amount of energy consumed to achieve a desired supply air temperature. AHU controller 330 can control the temperature of supply air 310 and/or building zone 306 by activating or deactivating coils 334-336, adjusting a speed of fan 338, or a combination of both.

Still referring to FIG. 3, in some embodiments, the airside system 300 may include a building management system (BMS) controller (not shown) (or space controller) and a client device (not shown) (or remote computing device). The BMS controller can include one or more computer systems (e.g., servers, supervisory controllers, subsystem controllers, etc.) that serve as system level controllers, application or data servers, head nodes, or master controllers for airside system 300, waterside system 200, HVAC system 100, and/or other controllable devices and/or systems that serve building 10. The BMS controller can communicate with multiple downstream building systems or subsystems (e.g., HVAC system 100, a security system, a lighting system, waterside system 200, etc.) via a communications link according to like or disparate protocols (e.g., LON, BACnet, etc.). In various embodiments, AHU controller 330 and BMS controller can be separate or integrated. In an integrated implementation, AHU controller 330 can be a software module configured for execution by a processor of BMS controller.

In some embodiments, AHU controller 330 receives information from BMS controller (e.g., commands, setpoints, operating boundaries, etc.) and provides information to BMS controller (e.g., temperature measurements, valve or actuator positions, operating statuses, diagnostics, etc.). For example, AHU controller 330 can provide BMS controller with temperature measurements from temperature sensors 362-364, equipment on/off states, equipment operating capacities, and/or any other information that can be used by BMS controller to monitor or control a variable state or condition within building zone 306. In other words, the AHU controller 330 functions as a sensor unit for the BMS controller.

Client device (not shown) can include one or more human-machine interfaces or client interfaces (e.g., graphical user interfaces, reporting interfaces, text-based computer interfaces, client-facing web services, web servers that provide pages to web clients, etc.) for controlling, viewing, or otherwise interacting with HVAC system 100, its subsystems, and/or devices. Client device can be a computer workstation, a client terminal, a remote or local interface, or any other type of user interface device. Client device can be a stationary terminal or a mobile device. For example, client device can be a desktop computer, a computer server with a user interface, a laptop computer, a tablet, a smartphone, a PDA, or any other type of mobile or non-mobile device. Client device can communicate with BMS controller and/or AHU controller 330 via a communications link.

Residential HVAC System

Figure 4:
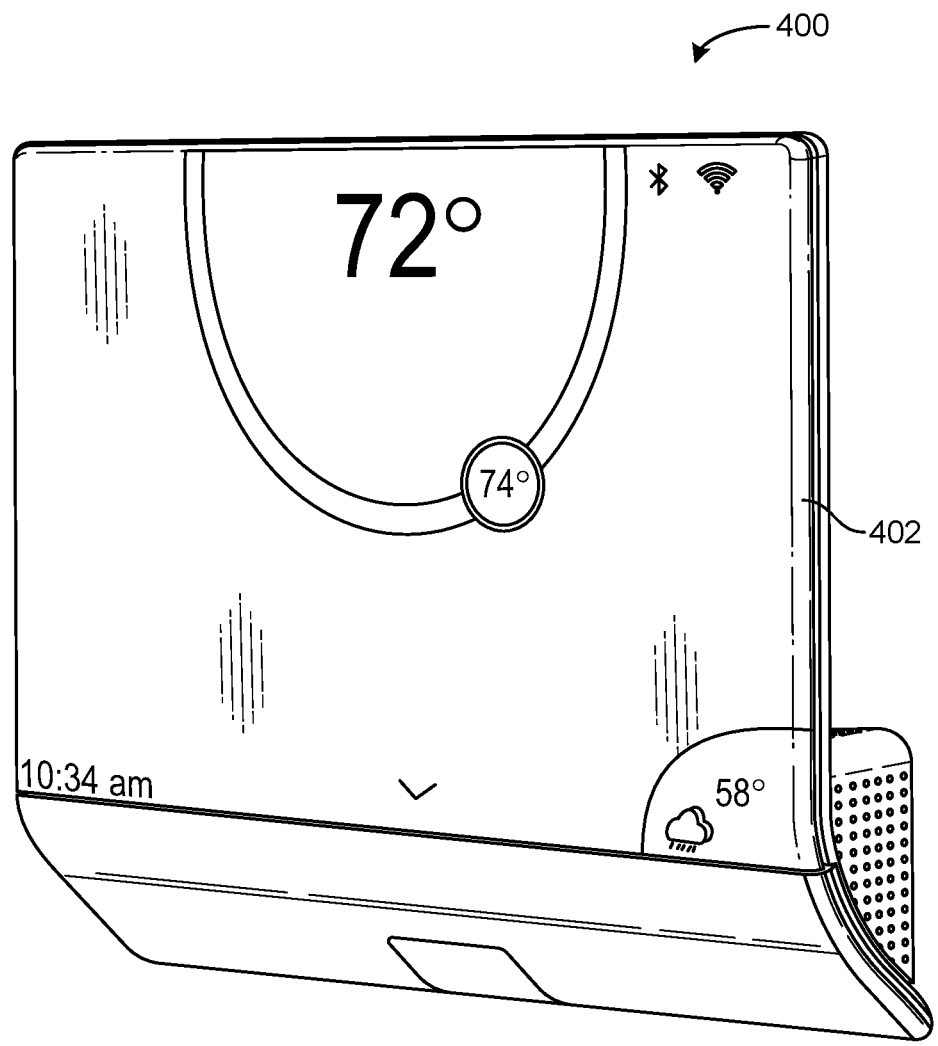
FIG. 4 is a drawing of a space controller with a transparent display, according to an exemplary embodiment.

Referring now to FIG. 4, a space controller for controlling building equipment and/or controlled devices is shown as thermostat 400, according to an exemplary embodiment. The thermostat 400 is shown to include a user interface, shown as display 402. The display 402 may be an interactive display that can display information to a user and receive input from the user. The display may be transparent such that a user can view information on the display and view the surface located behind the display. Thermostats with transparent and cantilevered displays are described in further detail in U.S. patent application Ser. No. 15/146,649 filed May 4, 2016, the entirety of which is incorporated by reference herein.

The display 402 can be a touchscreen or other type of electronic display configured to present information to a user in a visual format (e.g., as text, graphics, etc.) and receive input from a user (e.g., via a touch-sensitive panel). For example, the display 402 may include a touch-sensitive panel layered on top of an electronic visual display. A user can provide inputs through simple or multi-touch gestures by touching the display 402 with one or more fingers and/or with a stylus or pen. The display 402 can use any of a variety of touch-sensing technologies to receive user inputs, such as capacitive sensing (e.g., surface capacitance, projected capacitance, mutual capacitance, self-capacitance, etc.), resistive sensing, surface acoustic wave, infrared grid, infrared acrylic projection, optical imaging, dispersive signal technology, acoustic pulse recognition, or other touch-sensitive technologies known in the art. Many of these technologies allow for multi-touch responsiveness of display 402 allowing registration of touch in two or even more locations at once. The display may use any of a variety of display technologies such as light emitting diode (LED), organic light-emitting diode (OLED), liquid-crystal display (LCD), organic light-emitting transistor (OLET), surface-conduction electron-emitter display (SED), field emission display (FED), digital light processing (DLP), liquid crystal on silicon (LCoS), or any other display technologies known in the art. In some embodiments, the display 402 is configured to present visual media (e.g., text, graphics, etc.) without requiring a backlight.

Figure 5:
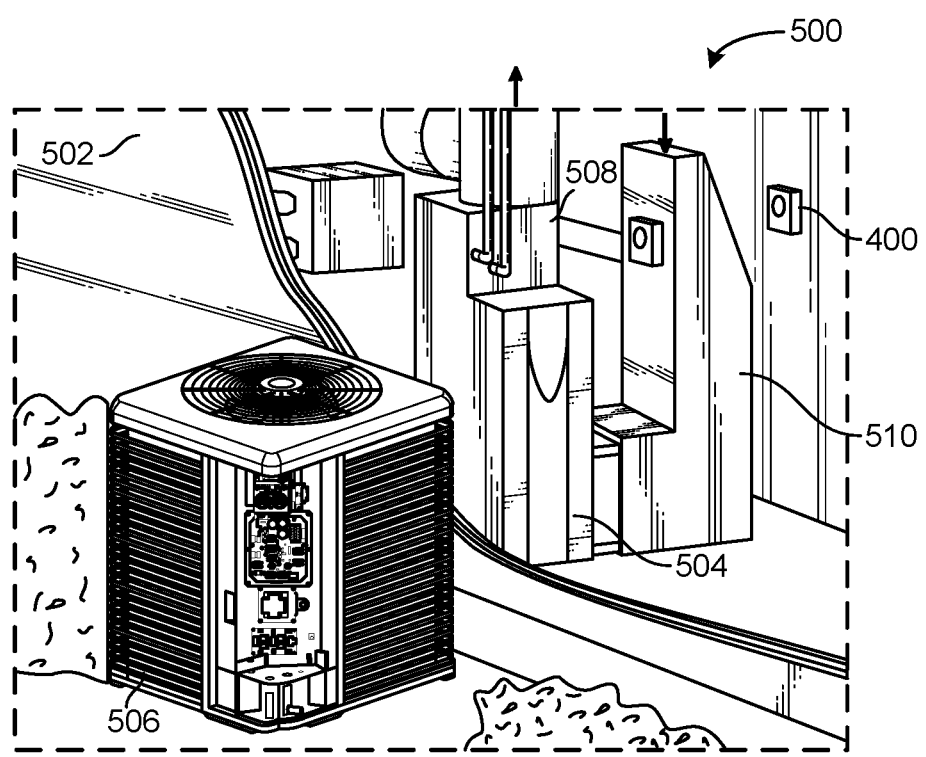
FIG. 5 is a schematic drawing of a building equipped with a residential heating and cooling system and the space controller of FIG. 4, according to an exemplary embodiment.

Referring now to FIG. 5, a residential heating and cooling system 500 is shown, according to an exemplary embodiment. The residential heating and cooling system 500 may provide heated and cooled air to a residential structure. Although described as a residential heating and cooling system 500, embodiments of the systems and methods described herein can be utilized in a cooling unit or a heating unit in a variety of applications include commercial HVAC units (e.g., roof top units). In general, a residence 502 includes refrigerant conduits that operatively couple an indoor unit 504 to an outdoor unit 506. Indoor unit 504 may be positioned in a utility space, an attic, a basement, and so forth. Outdoor unit 506 is situated adjacent to a side of residence 502. Refrigerant conduits transfer refrigerant between indoor unit 504 and outdoor unit 506, typically transferring primarily liquid refrigerant in one direction and primarily vaporized refrigerant in an opposite direction.

When the system 500 shown in FIG. 5 is operating as an air conditioner, a coil in outdoor unit 506 serves as a condenser for recondensing vaporized refrigerant flowing from indoor unit 504 to outdoor unit 506 via one of the refrigerant conduits. In these applications, a coil of the indoor unit 504, designated by the reference numeral 508, serves as an evaporator coil. Evaporator coil 508 receives liquid refrigerant (which may be expanded by an expansion device, not shown) and evaporates the refrigerant before returning it to outdoor unit 506.

Outdoor unit 506 draws in environmental air through its sides, forces the air through the outer unit coil using a fan, and expels the air. When operating as an air conditioner, the air is heated by the condenser coil within the outdoor unit 506 and exits the top of the unit at a temperature higher than it entered the sides. Air is blown over indoor coil 508 and is then circulated through residence 502 by means of ductwork 510, as indicated by the arrows entering and exiting ductwork 510. The overall system 500 operates to maintain a desired temperature as set by thermostat 400. When the temperature sensed inside the residence 502 is higher than the set point on the thermostat 400 (with the addition of a relatively small tolerance), the air conditioner will become operative to refrigerate additional air for circulation through the residence 502. When the temperature reaches the set point (with the removal of a relatively small tolerance), the unit can stop the refrigeration cycle temporarily.

In some embodiments, the system 500 configured so that the outdoor unit 506 is controlled to achieve a more elegant control over temperature and humidity within the residence 502. The outdoor unit 506 is controlled to operate components within the outdoor unit 506, and the system 500, based on a percentage of a delta between a minimum operating value of the compressor and a maximum operating value of the compressor plus the minimum operating value. In some embodiments, the minimum operating value and the maximum operating value are based on the determined outdoor ambient temperature, and the percentage of the delta is based on a predefined temperature differential multiplier and one or more time dependent multipliers.

Figure 6:
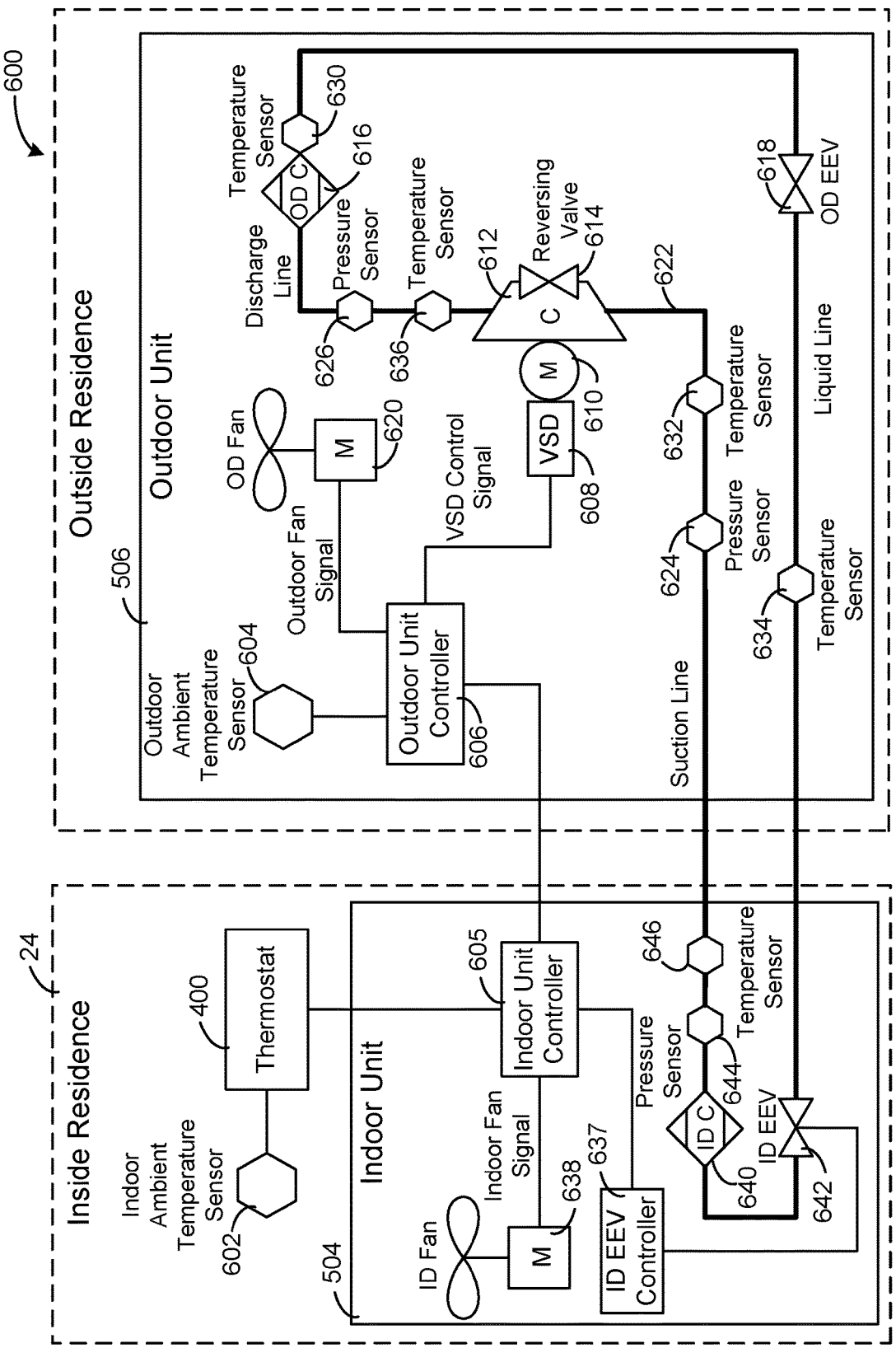
FIG. 6 is a schematic drawing of the space controller of FIG. 4 and the residential heating and cooling system of FIG. 5, according to an exemplary embodiment.

Referring now to FIG. 6, an HVAC system 600 is shown according to an exemplary embodiment. Various components of system 600 are located inside residence 502 while other components are located outside residence 502. Outdoor unit 506, as described with reference to FIG. 5, is shown to be located outside residence 502 while indoor unit 504 and thermostat 400, as described with reference to FIG. 6, are shown to be located inside the residence 502. In various embodiments, the thermostat 400 can cause the indoor unit 504 and the outdoor unit 506 to heat residence 502. In some embodiments, the thermostat 400 can cause the indoor unit 504 and the outdoor unit 506 to cool the residence 502. In other embodiments, the thermostat 400 can command an airflow change within the residence 502 to adjust the humidity within the residence 502.

Thermostat 400 can be configured to generate control signals for indoor unit 504 and/or outdoor unit 506. The thermostat 400 is shown to be connected to an indoor ambient temperature sensor 602, and an outdoor unit controller 606 is shown to be connected to an outdoor ambient temperature sensor 604. The indoor ambient temperature sensor 602 and the outdoor ambient temperature sensor 604 may be any kind of temperature sensor (e.g., thermistor, thermocouple, etc.). The thermostat 400 may measure the temperature of residence 502 via the indoor ambient temperature sensor 602. Further, the thermostat 400 can be configured to receive the temperature outside residence 502 via communication with the outdoor unit controller 606. In various embodiments, the thermostat 400 generates control signals for the indoor unit 504 and the outdoor unit 506 based on the indoor ambient temperature (e.g., measured via indoor ambient temperature sensor 602), the outdoor temperature (e.g., measured via the outdoor ambient temperature sensor 604), and/or a temperature set point.

The indoor unit 504 and the outdoor unit 506 may be electrically connected. Further, indoor unit 504 and outdoor unit 506 may be coupled via conduits 622. The outdoor unit 506 can be configured to compress refrigerant inside conduits 622 to either heat or cool the building based on the operating mode of the indoor unit 504 and the outdoor unit 506 (e.g., heat pump operation or air conditioning operation). The refrigerant inside conduits 622 may be any fluid that absorbs and extracts heat. For example, the refrigerant may be hydro fluorocarbon (HFC) based R-410A, R-407C, and/or R-134a.

The outdoor unit 506 is shown to include the outdoor unit controller 606, a variable speed drive 608, a motor 610 and a compressor 612. The outdoor unit 506 can be configured to control the compressor 612 and to further cause the compressor 612 to compress the refrigerant inside conduits 622. In this regard, the compressor 612 may be driven by the variable speed drive 608 and the motor 610. For example, the outdoor unit controller 606 can generate control signals for the variable speed drive 608. The variable speed drive 608 (e.g., an inverter, a variable frequency drive, etc.) may be an AC-AC inverter, a DC-AC inverter, and/or any other type of inverter. The variable speed drive 608 can be configured to vary the torque and/or speed of the motor 610 which in turn drives the speed and/or torque of compressor 612. The compressor 612 may be any suitable compressor such as a screw compressor, a reciprocating compressor, a rotary compressor, a swing link compressor, a scroll compressor, or a turbine compressor, etc.

In some embodiments, the outdoor unit controller 606 is configured to process data received from the thermostat 400 to determine operating values for components of the system 600, such as the compressor 612. In one embodiment, the outdoor unit controller 606 is configured to provide the determined operating values for the compressor 612 to the variable speed drive 608, which controls a speed of the compressor 612. The outdoor unit controller 606 is controlled to operate components within the outdoor unit 506, and the indoor unit 504, based on a percentage of a delta between a minimum operating value of the compressor and a maximum operating value of the compressor plus the minimum operating value. In some embodiments, the minimum operating value and the maximum operating value are based on the determined outdoor ambient temperature, and the percentage of the delta is based on a predefined temperature differential multiplier and one or more time dependent multipliers.

In some embodiments, the outdoor unit controller 606 can control a reversing valve 614 to operate system 600 as a heat pump or an air conditioner. For example, the outdoor unit controller 606 may cause reversing valve 614 to direct compressed refrigerant to the indoor coil 508 while in heat pump mode and to an outdoor coil 616 while in air conditioner mode. In this regard, the indoor coil 508 and the outdoor coil 616 can both act as condensers and evaporators depending on the operating mode (i.e., heat pump or air conditioner) of system 600.

Further, in various embodiments, outdoor unit controller 606 can be configured to control and/or receive data from an outdoor electronic expansion valve (EEV) 618. The outdoor electronic expansion valve 618 may be an expansion valve controlled by a stepper motor. In this regard, the outdoor unit controller 606 can be configured to generate a step signal (e.g., a PWM signal) for the outdoor electronic expansion valve 618. Based on the step signal, the outdoor electronic expansion valve 618 can be held fully open, fully closed, partial open, etc. In various embodiments, the outdoor unit controller 606 can be configured to generate step signal for the outdoor electronic expansion valve 618 based on a subcool and/or superheat value calculated from various temperatures and pressures measured in system 600. In one embodiment, the outdoor unit controller 606 is configured to control the position of the outdoor electronic expansion valve 618 based on a percentage of a delta between a minimum operating value of the compressor and a maximum operating value of the compressor plus the minimum operating value. In some embodiments, the minimum operating value and the maximum operating value are based on the determined outdoor ambient temperature, and the percentage of the delta is based on a predefined temperature differential multiplier and one or more time dependent multipliers.

The outdoor unit controller 606 can be configured to control and/or power outdoor fan 620. The outdoor fan 620 can be configured to blow air over the outdoor coil 616. In this regard, the outdoor unit controller 606 can control the amount of air blowing over the outdoor coil 616 by generating control signals to control the speed and/or torque of outdoor fan 620. In some embodiments, the control signals are pulse wave modulated signals (PWM), analog voltage signals (i.e., varying the amplitude of a DC or AC signal), and/or any other type of signal. In one embodiment, the outdoor unit controller 606 can control an operating value of the outdoor fan 620, such as speed, based on a percentage of a delta between a minimum operating value of the compressor and a maximum operating value of the compressor plus the minimum operating value. In some embodiments, the minimum operating value and the maximum operating value are based on the determined outdoor ambient temperature, and the percentage of the delta is based on a predefined temperature differential multiplier and one or more time dependent multipliers.

The outdoor unit 506 may include one or more temperature sensors and one or more pressure sensors. The temperature sensors and pressure sensors may be electrical connected (i.e., via wires, via wireless communication, etc.) to the outdoor unit controller 606. In this regard, the outdoor unit controller 606 can be configured to measure and store the temperatures and pressures of the refrigerant at various locations of the conduits 622. The pressure sensors may be any kind of transducer that can be configured to sense the pressure of the refrigerant in the conduits 622. The outdoor unit 506 is shown to include pressure sensor 624. The pressure sensor 624 may measure the pressure of the refrigerant in conduit 622 in the suction line (i.e., a predefined distance from the inlet of compressor 612). Further, the outdoor unit 506 is shown to include pressure sensor 626.

The pressure sensor 626 may be configured to measure the pressure of the refrigerant in conduits 622 on the discharge line (e.g., a predefined distance from the outlet of compressor 612).

The temperature sensors of outdoor unit 506 may include thermistors, thermocouples, and/or any other temperature sensing device. The outdoor unit 506 is shown to include temperature sensor 630, temperature sensor 632, temperature sensor 634, and temperature sensor 636. The temperature sensors (i.e., temperature sensor 630, temperature sensor 632, temperature sensor 634, and/or temperature sensor 636) can be configured to measure the temperature of the refrigerant at various locations inside conduits 622.

Referring now to the indoor unit 504, the indoor unit 504 is shown to include indoor unit controller 605, indoor electronic expansion valve controller 637, an indoor fan 638, an indoor coil 640, an indoor electronic expansion valve 642, a pressure sensor 644, and a temperature sensor 646. The indoor unit controller 605 can be configured to generate control signals for indoor electronic expansion valve controller 637. The signals may be set points (e.g., temperature set point, pressure set point, superheat set point, subcool set point, step value set point, etc.). In this regard, indoor electronic expansion valve controller 637 can be configured to generate control signals for indoor electronic expansion valve 642. In various embodiments, indoor electronic expansion valve 642 may be the same type of valve as outdoor electronic expansion valve 618. In this regard, indoor electronic expansion valve controller 637 can be configured to generate a step control signal (e.g., a PWM wave) for controlling the stepper motor of the indoor electronic expansion valve 642. In this regard, indoor electronic expansion valve controller 637 can be configured to fully open, fully close, or partially close the indoor electronic expansion valve 642 based on the step signal.

Indoor unit controller 605 can be configured to control indoor fan 638. The indoor fan 638 can be configured to blow air over indoor coil 640. In this regard, the indoor unit controller 605 can control the amount of air blowing over the indoor coil 640 by generating control signals to control the speed and/or torque of the indoor fan 638. In some embodiments, the control signals are pulse wave modulated signals (PWM), analog voltage signals (i.e., varying the amplitude of a DC or AC signal), and/or any other type of signal. In one embodiment, the indoor unit controller 605 may receive a signal from the outdoor unit controller indicating one or more operating values, such as speed for the indoor fan 638. In one embodiment, the operating value associated with the indoor fan 638 is an airflow, such as cubic feet per minute (CFM). In one embodiment, the outdoor unit controller 606 may determine the operating value of the indoor fan based on a percentage of a delta between a minimum operating value of the compressor and a maximum operating value of the compressor plus the minimum operating value. In some embodiments, the minimum operating value and the maximum operating value are based on the determined outdoor ambient temperature, and the percentage of the delta is based on a predefined temperature differential multiplier and one or more time dependent multipliers.

The indoor unit controller 605 may be electrically connected (e.g., wired connection, wireless connection, etc.) to pressure sensor 644 and/or temperature sensor 646. In this regard, the indoor unit controller 605 can take pressure and/or temperature sensing measurements via pressure sensor 644 and/or temperature sensor 646. In one embodiment, pressure sensor 644 and temperature sensor 646 are located on the suction line (i.e., a predefined distance from indoor coil 640). In other embodiments, the pressure sensor 644 and/or the temperature sensor 646 may be located on the liquid line (i.e., a predefined distance from indoor coil 640).

Personal Health Monitoring System

Figure 7:
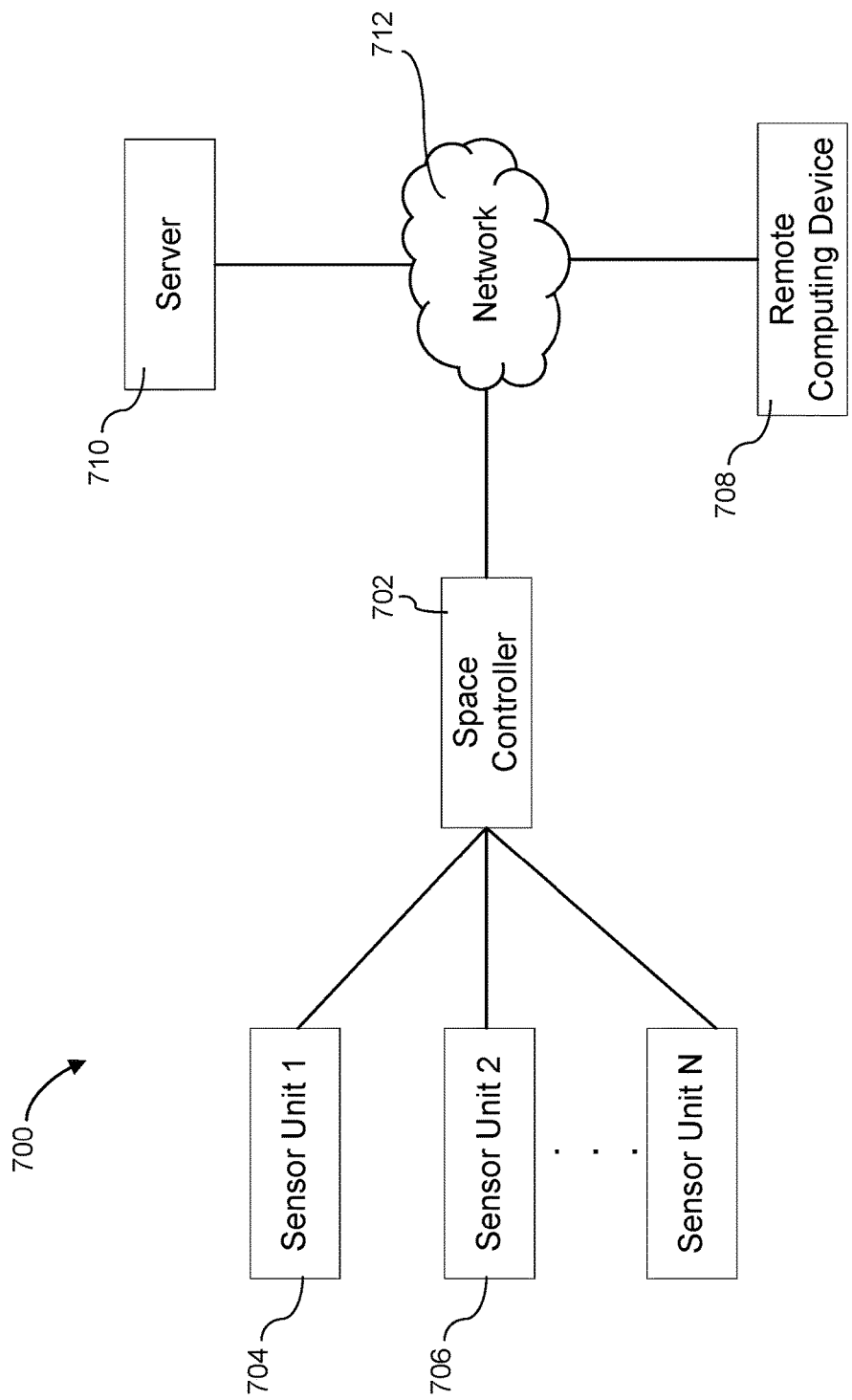
FIG. 7 is a block diagram of a personal health monitoring system for a building, according to an exemplary embodiment.

Referring to FIG. 7, a personal health monitoring system 700 is shown that may be implemented within a building (e.g., building 10, residence 502), according to an exemplary embodiment. The system 700 is configured to measure and report health values and/or metrics associated with an occupant of the building. More specifically, the system 700 is configured to measure and report health metrics in two modes of operation, a first mode in which the system 700 measures a first health metric (e.g., air quality) within a space in which the system 700 is located, and a second mode of operation in which the system 700 measures a second health metric relating to a person's health (e.g., blood alcohol content, etc.). The first health metric may be measured continuously within the space (e.g., by measuring air quality of quiescent air within the space), while the second health metric may be measured over a predefined time interval. For example, the predefined time interval may be an amount of time required for a person to completely exhale air from their lungs in close proximity to the system 700 (e.g., a time it takes for a person to blow out a volume of air from their lungs over an air quality and/or VOC sensor).

The system 700 includes a space controller 702 and a plurality of sensor units communicably coupled to the space controller 702. Each of the plurality of sensor units may be disposed remotely from one another (and from the space controller) in a different location within the building. For example, a first sensor unit 704 of the plurality of sensor units may be disposed within a first room of a building. A second sensor unit 706 of the plurality of sensor units may be disposed in a second room of a building. In some embodiments, the sensor units may be disposed in different regions or spaces within the same room. The sensor units may include a communications interface configured to provide wireless (e.g., Bluetooth, WiFi/radio, etc.) connectivity between the sensor units and the space controller 702.

The sensor unit 704 is configured to measure and report sensor data and other information to the space controller 702. The sensor unit 704 may be a trimmed down version of the space controller 702. In various exemplary embodiments, the sensor unit 704 may be a smart speaker or an edge computing device (e.g., an edge sensor, etc.). The sensor unit 704 may include onboard sensors including an air quality sensor. The sensor unit 704 may additionally include a processing circuit and memory, and may be configured to determine various health values/metrics based on the sensor data received from the onboard sensors. In some embodiments, the sensor unit 704 may be configured to generate notifications based on the sensor data and/or the determined health values. The sensor unit 704 may be configured to transmit the sensor data, health values, and/or notifications to the space controller 702 via the communications interface.

As shown in FIG. 7, the space controller 702 is communicably coupled to a remote computing device 708 and a server 710 via network 712. Each of the space controller 702, the remote computing device 708, and the server 710 may be configured to communicate (e.g., send and/or receive data) among each other via the network 712. The remote computing device 708 may be the same as or similar to the client device described with reference to FIG. 3. The remote computing device 708 may be a smartphone, a tablet, a laptop computer, a desktop computer, and/or any other user device for reviewing interfaces and receiving user input. The server 710 may be a cloud computing device and may include memory configured to store data from the space controller 702 and/or the remote computing device 708. The server 710 may be located remotely from the building. In some embodiments, the server 710 may be communicably coupled to multiple space controllers 702 and/or remote computing devices 708 from different buildings. In some embodiments, the network 712 is at least one of and/or a combination of a Wi-Fi network, a wired Ethernet network, a Zigbee network, a Bluetooth network, and/or any other wireless and/or wired network. In other embodiments, the network 712 may be a local area network and/or a wide area network (e.g., the Internet, a building WAN, etc.) and may use a variety of communications protocols (e.g., BACnet, IP, LON, etc.). The network 712 may include routers, modems, and/or network switches. In some embodiments, the network 712 may be a combination of wired and wireless networks.

Figure 8:
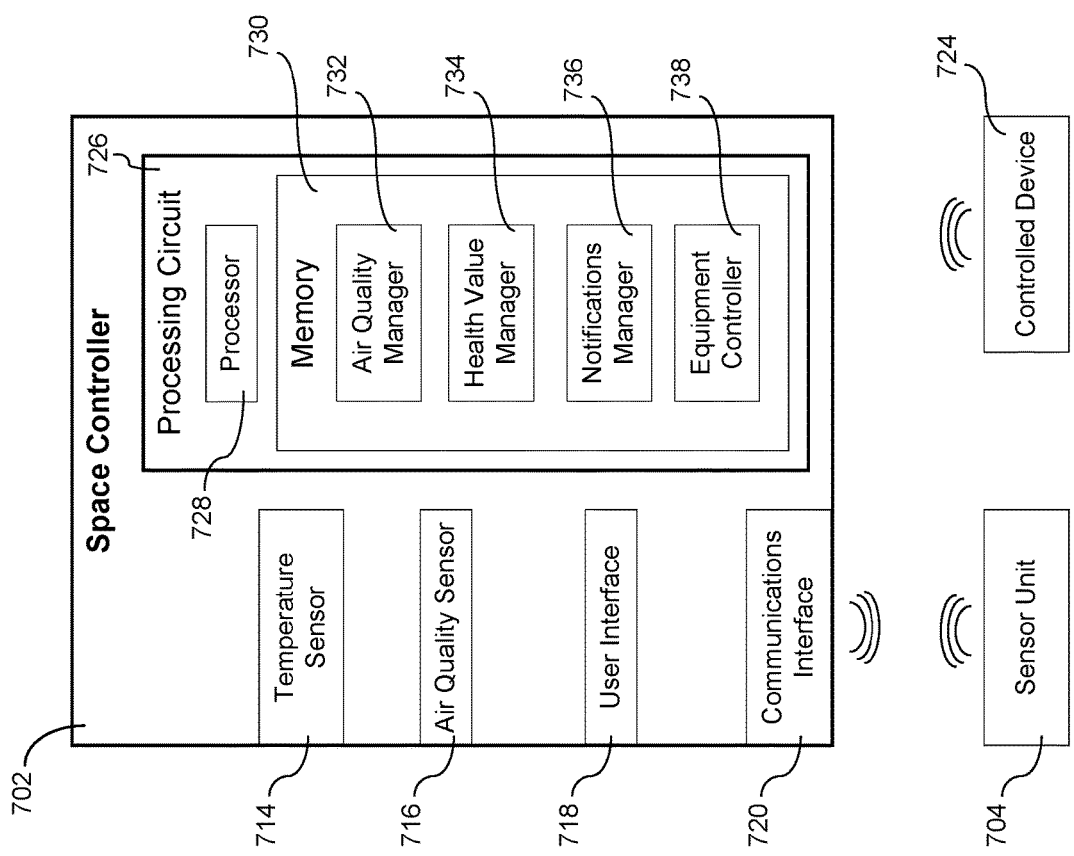
FIG. 8 is a block diagram of a space controller for the personal health monitoring system of FIG. 7, according to an exemplary embodiment.

Referring now to FIG. 8, a block diagram of a space controller 702 is shown, according to an exemplary embodiment. The space controller 702 includes a plurality of sensors onboard the space controller 702 (e.g., contained within the same housing or enclosure as the space controller 702, etc.). The space controller 702 is shown to include a temperature sensor 714, an air quality sensor 716, a proximity sensor 717, and a thermal imager 719. The temperature sensor 714 is configured to measure a temperature of the room or space where the space controller is located. The air quality sensor 716 is configured to measure an air quality (e.g., an amount of VOCs, CO2, CO, etc.) within the vicinity of the space controller 702. The air quality sensor 716 may be configured to measure air quality data from a space or room in which the space controller 702 is located and/or from air blown or otherwise exhausted directly over the air quality sensor 716. The proximity sensor 717 configured to determine a distance between a user and the space controller 702 (e.g., whether a person is within a predefined range of the space controller 702, etc.). The proximity sensor 717 may include one of a capacitive proximity sensor, a photoelectric proximity sensor, or another type of sensing device configured to determine a distance between objects and the sensor. The thermal imager 719 is configured to determine the surface temperature of objects and/or the environment surrounding the space controller 702. For example, the thermal imager 719 may be an infrared (IR) camera. In other embodiments, the thermal imager 719 may be a forehead temperature scanner (e.g., a temporal thermometer, etc.) configured to determine a person's body temperature when in contact with the person's forehead or other surface of the user. In other embodiments, the space controller 702 may include additional, fewer, and/or different sensors. For example, the space controller 702 may include a first air quality sensor configured to measure air quality data from a from a space or room in which the space controller 702 is located in a first mode of operation and a second air quality sensor to measure air quality data from air blown or otherwise exhausted directly over the air quality sensor in a second mode of operation. The space controller 702 is also shown to include a user interface 718, which may be the same as or similar to the user interface 402 described with reference to FIG. 4.

In some embodiments, the space controller 702 is a thermostat (e.g., a "smart" thermostat 400 as shown in FIG. 4) and is configured to operate a controlled device to maintain a temperature of the space within a predefined temperature range. For example, the user interface 402 may be configured to receive input from a user including a temperature preference. The thermostat may be configured to operate HVAC equipment to heat or cool the space to maintain the temperature to within a predefined range above and/or below the temperature preference. The HVAC equipment may include an air conditioning unit, a heater, a fan, a damper position, a smart vent, or another form of HVAC equipment.

In other embodiments, the space controller 702 is another type of wired or wireless controller configured to operate a controlled device 724. For example, the space controller 702 may be a smart hub, a home hub, a security system control unit, or another computing device located within the building.

As shown in FIG. 8, the space controller 702 additionally includes a communications interface 720. In various exemplary embodiments, the communications interface 720 is configured for bi-direction communication with the network 712 (see FIG. 6) and a sensor unit 704. In other words, the communications interface 720 is configured to both transmit data to and receive data from the network 712 and the sensor unit 704. For example, the communications interface 720 may be configured to communicate sensor data and/or other information received from the sensor unit 704 to the remote computing device 708 and/or server 710 via the network 712. The sensor data may include air quality data from the air quality sensor 716 or other health values/metrics determined by the space controller 702.

In some embodiments, the communications interface 720 is also configured for bi-directional communication with a controlled device 724. The space controller 702 may be configured to operate the controlled device 724 based on sensor data from any one of the plurality of onboard sensors. In some embodiments, the controlled device 724 may include building automation equipment. For example, the controlled device 724 may be i) a door lock of a door between rooms within the building (e.g., a lab space, a workshop, etc.), ii) a door lock for an exterior door of the building (e.g., a front door, a garage door, a vehicle access door, etc.), iii) a security system (e.g., an alarm for the security system, a camera associated with the security system, etc.), or iv) an HVAC system (e.g., an air conditioning unit, a heating unit, a smart vent or damper, a fan, etc.). In other embodiments, the controlled device 724 may include user operated equipment and/or other equipment that is remotely connected to the space controller 702 via the communications interface 720 and/or network 712 (see FIG. 6). For example, the controlled device 724 may include a door lock or other locking device for a piece of equipment in proximity to the building (e.g., a vehicle such as a smart car or truck, a forklift, etc.) or an ignition control system for the piece of equipment. In other embodiments, the controlled device 724 may include any other type of remotely operable equipment.

The space controller 702 is shown to include a processing circuit 726 including a processor 728, and a memory 730. The processor 728 can be implemented as a general purpose processor, an application specific integrated circuit (ASIC), one or more field programmable gate arrays (FPGAs), a group of processing components, or other suitable electronic processing components. The memory 730 (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present application. The memory 730 can be or include volatile memory or non-volatile memory. The memory 730 can include object code components, script components, or any other type of information structure for supporting the various activities and information structures described in the present application. According to some embodiments, the memory 730 is communicably connected to the processor 728 via the processing circuit 726 and can include computer code for executing (e.g., by the processing circuit 726 and/or the processor 728) one or more processes and/or functionalities described herein.

In the embodiment of FIG. 8, the memory 730 is shown to include an air quality manager 732. The air quality manager 732 may be configured to communicate with an air quality sensor 716 onboard the space controller 702 to receive air quality data associated with the space in which the space controller 702 is located (and/or with the air incident on the air quality sensor 132). The air quality data can include humidity, relative humidity, volatile organic compounds (VOCs), carbon dioxide (CO2), carbon monoxide (CO) an air quality index (AQI), and/or any other data that is associated with the space and/or air in proximity to the air quality sensor 132. The air quality manager 732 may be configured to display the air quality data to a user via the user interface 718 (e.g., display, etc.).

The memory 730 is also shown to include a health value manager 734. The health value manager 734 may be configured to determine a health value (e.g., a health metric) based on the air quality data received from the air quality manager 732 (e.g., from the onboard air quality sensor 716 and/or thermal imager 719). The health value may include biometric values for an occupant of the space. For example, the health value may include a skin temperature of the occupant of the space based on sensor data from the thermal imager 719, or a body temperature determined by applying a predefined correction value to the data (e.g., a correction factor based on empirical measurements comparing skin temperature data to a person's actual body temperature). The health value manager 734 may be configured to determine whether the occupant has a fever based on the data received from the thermal imager 719; for example, by comparing the data with a threshold skin temperature in memory 730.

In other embodiments, the health value may include a blood alcohol content (BAC) of the occupant based on a value for VOCs that is measured within the space (and/or on the air incident on the air quality sensor 716 from the occupant breathing onto the air quality sensor 716). The value for VOCs may be an amount of ethanol or ethanol content of the air. In other embodiments, the health value may be associated with an amount of CO, NO, H2S, acetone, and/or other gasotransmitters or compounds exhaled by the occupant or by a plurality of occupants within the space. In other embodiments, the health value may include an air quality indicative of a condition in the space. For example, the health value may be an average amount of CO, CO2, VOCs, or another chemical compound within the space. The memory 730 is also shown to include a notifications manager 736. The notifications manager 736 may be configured to generate a notification based on one, or a combination of, the air quality data from the air quality manager 732 (e.g., air quality sensor 716) and the health value from the health value manager 734. For example, the notifications manager 736 may be configured to generate a notification indicating the BAC of the occupant/user or other health value of the occupant/user determined by the health value manager 734. The notifications manager 736 may be configured to display the notification via the user interface 718 of the space controller 702 to inform a user of the associated health value. In some embodiments, the notification is a message indicating the health value (e.g., "BAC=0.1", etc.). In other embodiments, the notification is an alert that a threshold value has been exceeded (e.g., that the occupant/user is in poor health that the BAC of the occupant/user is exceeds predefined thresholds, etc.). In some embodiments, the threshold value is a BAC or another health value that, once exceeded, results in remedial action by the space controller 702 to prevent the user from performing certain activities, as will be further described. In various exemplary embodiments, the notification includes a graphic (e.g., a smiley face indicating the health value is within a desired range, etc.). Alternatively, or in combination, the graphic may include a light (e.g., an LED) that changes color depending on the health value (e.g., a green light indicating the health value is within a desired range, etc.).

The memory 730 is also shown to include an equipment controller 738. The equipment controller 738 may be configured to control the operation of the controlled device 724 based on one, or a combination of, sensor data from the air quality sensor 716 or air quality manager 732, a health value from the health value manager 734, and a notification from the notifications manager 736. For example, the equipment controller 738 may be configured to operate the controlled device 724 based on a determination (from the health value manager 734) that the BAC of the occupant exceeds a predefined threshold. The equipment controller 738 may be configured to generate a control signal activate and/or deactivate the controlled device 724; for example, the equipment controller 738 may be configured generate a control signal to activate and/or deactivate door locks within the building, which, advantageously, may prevent the occupant from entering a lab space or an industrial workspace (e.g., a machine shop, a manufacturing building, etc.) when the occupant is intoxicated. In other embodiments, the equipment controller 738 may be configured to generate a control signal to lockout a vehicle such as a car, truck, forklift, etc. Among other benefits, selectively restricting access to different rooms and/or user operated equipment may prevent the occupant from injuring themselves or others (e.g., due to reduced coordination from excessive drinking, etc.).

The processing circuit 726 may be configured to transmit information (e.g., sensor data, health values, notifications, etc.) from the air quality manager 732, the health value manager 734, the notifications manager 736, and the equipment controller 738 to the server 710 and/or the remote computing device 708. The information may be accessed through a software application (e.g., an app on a mobile phone, a laptop computer, etc.), which may be integrated with services such as If This Then That (IFTTT), Stringify, and/or other web-based applications/services to help make logic decisions based on the information. In some embodiments, the information may be used by software to operate controlled devices that aren't directly connected to the space controller 702 (e.g., to control web-services, etc.). For example, the information may be used to selectively restrict an occupant of the space from accessing certain online databases based on their BAC. For example, the information may be used to prevent an occupant with a BAC above a threshold value (e.g., a legal alcohol limit for a jurisdiction, state, or country) from accessing financial information (e.g., from logging into an online banking account, from making a financial transaction through a banking or money transfer service, etc.). In other embodiments, the information may be used to prevent an application to prevent the occupant from communicating with select individuals based on their BAC (e.g., by restricting access to a text messaging service, to a social media service, etc.). In yet other embodiments, the information (e.g., BAC, etc.) may be accessed through an application by law enforcement officials for monitoring individuals on parole.

The processing circuit 726 may also be configured to operate the space controller 702 in multiple modes of operation. For example, in a first mode of operation, the processing circuit 726 may be configured to operate the air quality sensor to determine an average condition (e.g., air quality) within the space in which the space controller 702 is located. In the first mode of operation, the processing circuit 726 may be configured to operate the air quality sensor continuously while the space controller 702 is activated (i.e., powered on) to obtain a real-time value of the air quality within the space. In a second mode of operation, the processing circuit 726 may be configured to determine a health metric that is indicative of a person's health. The health metric may be a blood alcohol content (BAC) value, another psychoactive substance present on a person's breath, and/or another metric indicative of medical problems that result in disturbances in psychophysiological functions and responses. In the second mode of operation, the processing circuit 726 may be configured to receive air quality data from the air quality sensor over a predefined time interval. The predefined time interval may be a period of time that is approximately equal to an average amount of time it takes a person to completely exhale a full volume of air from his/her lungs over the air quality sensor (e.g., to blow onto the air quality sensor).

Figure 9A:
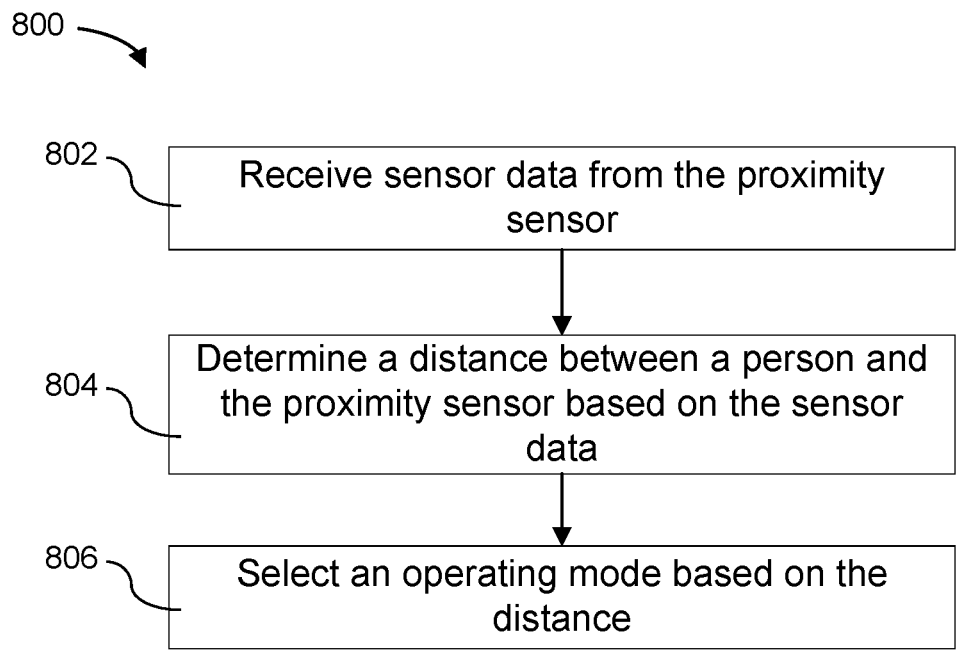
FIG. 9A is a flow diagram of a method of selecting an operating mode of a sensor unit and/or space controller, according to an exemplary embodiment.

The processing circuit 726 may be configured to switch between the first operating mode and the second operating mode. For example, a user may be able to select the desired operating mode from the user interface (e.g., via the touch sensitive display 402 of FIG. 4, etc.). In other words, the space controller 702 may be configured to operate in one of the first operating mode and the second operating mode based on user input. In other embodiments, the operating mode may be determined based on sensor data received from the proximity sensor 717. For example, the space controller 702 may be configured to switch to the second mode of operation based on sensor data from the proximity sensor 717 indicating a person is within a predefined range (e.g., distance) of the space controller 702 (e.g., 1 ft., 2 ft., etc.). FIG. 9A shows a flow diagram of a method 800 of selecting an operating mode using the proximity sensor 719, according to an exemplary embodiment. The space controller and the controlled device may be the same or similar to the space controller 702 and controlled device 724 described with reference to FIGS. 7-8. At 802, sensor data is received from the proximity sensor 719. The sensor data may include a voltage that is proportional to a distance between a nearest surface of a person (e.g., a person's clothing, skin, etc.) and the proximity sensor 719. At 804, the sensor unit and/or space controller determines a distance between a person and the proximity sensor based on the sensor data. Operation 804 may include applying a correction factor to the sensor data to convert the voltage to a distance in feet, inches, etc. In other embodiments, operation 804 includes converting to the voltage to a distance by stepping through a table of predefined voltages and corresponding values of distance. In yet other embodiments, the sensor unit and/or space controller may use the voltage values directly to determine whether the operating mode should be switched. At 806, the sensor unit and/or space controller selects an operating mode based on the distance. Operation 806 may include switching to the second mode of operation based on a determination that the distance is below a predefined threshold value (e.g., 1 ft., 2 ft., etc.), or switching to the first mode of operation based on a determination that the distance is greater than the predefined threshold value. In other embodiments, method 800 may include additional, fewer, and/or different operations.

In other embodiments, the processing circuit 726 may be configured to operate multiple air quality sensors simultaneously to obtain average air quality data from the space and also air quality data from the micro-environment created by a user by blowing onto the air quality sensor.

Figure 9B:
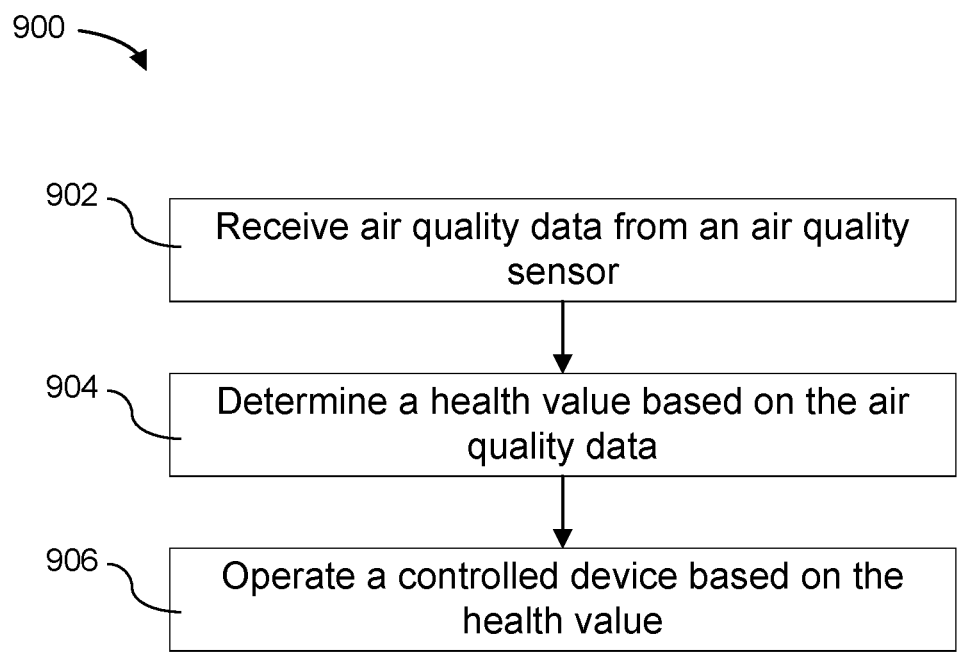
FIG. 9B is a flow diagram of a method of operating a controlled device using air quality data from an air quality sensor, according to an exemplary embodiment.

Referring to FIG. 9B, a flow diagram of a method 900 of operating a controlled device by a space controller is shown, according to an exemplary embodiment. The space controller and the controlled device may be the same or similar to the space controller 702 and controlled device 724 described with reference to FIGS. 7-8. At 902, air quality data is received from an air quality sensor (e.g., air quality sensor 716) that is located within a building. The air quality sensor may be positioned onboard a sensor unit (e.g., coupled to the housing or enclosure for the sensor unit) or onboard the space controller 702. Operation 902 may include sampling air from a room with multiple occupants to obtain air quality data for the room (e.g., average air quality based on the quiescent air quality measured by the air quality sensor). In some embodiments, operation 902 includes sampling air from within the room or space continuously to obtain a real-time measurement of the air quality within the space (or average air quality). In other embodiments, operation 902 includes receiving air from an occupant of a room or space where the space controller (and/or sensor unit) is located (e.g., in a second mode of operation). For example, the occupant may exhale directly onto the air quality sensor or in close proximity to the air quality sensor. In some embodiments, operation 902 includes sampling the air over a predefined time interval (e.g., an occupant presses a button to notify the space controller that a sample is being provided and the space controller activates the air quality sensor for the predefined time interval after the button is depressed, etc.). The air quality data may include a value for VOCs such as an ethanol content of the air or another gasotransmitter. In some embodiments, the air quality data includes a hydrogen content of the air, an amount of $CO_2$, or another parameter indicative of the health of the occupant(s).

At 904, the sensor unit and/or space controller determines a health value based on the air quality data received from the air quality sensor. For example, the space controller (e.g., the health value manager 734) may use the gasotransmitter data to determine whether the occupant has smoke on their breath by comparing the gasotransmitter data to threshold values (e.g., baseline values based on experimental data from individuals who are not currently smoking, etc.). In some embodiments, the health value may be an overall wellness metric that is proportional to the differences between measured values of gasotransmitters to empirical data for healthy individuals. In other embodiments, the health value is indicative of a condition of the space within which the air quality sensor is located. For example, the health value may be indicative of an amount of $CO_2$ or other gaseous compounds in a gym environment, where multiple occupants may be breathing heavily, working out, etc.

In some embodiments, the health value is determined based on historical information (e.g., historical air quality data, etc.). In such an embodiment, operation 904 may include analyzing the historical air quality data to identify trends that may be a sign of a serious problem (e.g., continuously high levels of certain gasotransmitters over a predefined interval of time).

At 906, the space controller (and/or remote computing device 708 described with reference to FIG. 7) operates a controlled device based on the health value. Operation 906 may include comparing the health value (or air quality data) to a threshold value and generating a control signal to operate the controlled device based on a determination that the health value is above or below the threshold value. For example, operation 906 may include transmitting a control signal via a communications interface of the space controller to an HVAC system based on a determination that an amount of $CO_2$, CO, or another gaseous compound exceeds a predefined threshold. The control signal may cause activation of an air conditioning unit, a heater, a fan, a smart vent, a damper, etc. to circulate air within the space to return the air quality to within acceptable levels. In some embodiments, operation 906 may further include generating a notification indicative of the health value (e.g., an alert that the air quality within the space is poor). Operation 906 may further include reporting the notification to an occupant of the space by displaying the notification on the user interface.

Figure 10:
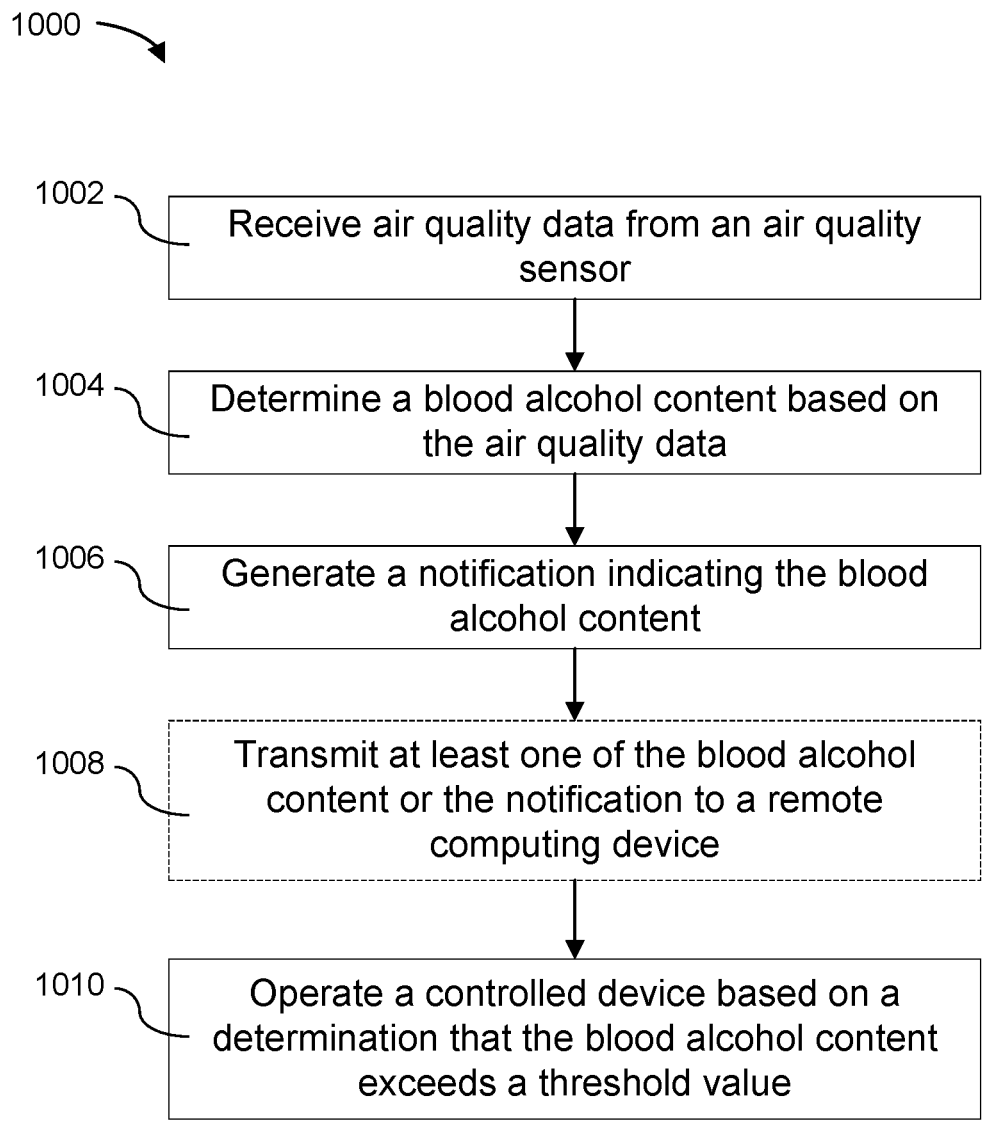
FIG. 10 is a flow diagram of a method of operating a controlled device based on a blood alcohol content determined using an air quality sensor, according to an exemplary embodiment.

Referring now to FIG. 10, a flow diagram of a method 1000 of operating a controlled device based on a BAC value determined using a space controller within a building is shown, according to an exemplary embodiment. Although the method 1000 is described with reference to determining a BAC value, it should be appreciated that the health value determined by the method 1000 may be different in other embodiments (e.g., another psychoactive substance present on a person's breath). Again, the space controller and the controlled device may be the same or similar to the space controller 702 and controlled device 724 described with reference to FIGS. 7-8. At 1002, air quality data is received from an air quality sensor. Operation 1002 may be the same or similar to operation 902 of FIG. 9B. In various exemplary embodiments, operation 1002 includes receiving a value for VOCs from the air quality controller. More specifically, operation 1002 may include receiving an ethanol content of air in proximity to the air quality sensor and measuring the ethanol content of air from a sample volume (a fixed volume quantity provided by the occupant).

At 1004, the space controller (and/or sensor unit) determines a BAC based on the air quality data. Operation 1004 may include scaling a measured concentration of ethanol in the air (e.g., a concentration of ethanol in an occupant's breath) with a predefined relativity ratio of breath alcohol to blood alcohol (e.g., a 2,100:1 or another predefined concentration of breath alcohol to equivalent blood alcohol). Operation 1004 may further include converting the determined blood alcohol in mL concentration to a percentage BAC (e.g., 0.05%, 0.1%, etc.).

At 1006, the space controller (and/or sensor unit) generates a notification indicating the BAC. Operation 1006 may include displaying the percentage BAC via the user interface of the space controller. Operation 1006 may additionally include generating an alert notifying the occupant that the percentage BAC exceeds predefined thresholds (e.g., displaying a graphic, illuminating a red light, or displaying a warning message). For example, the space controller may report a warning message to the occupant indicating that the measured BAC exceeds legal limits for operating motor vehicles, etc.

At 1008, the space controller optionally transmits one, or a combination of, the BAC and the notification to a remote computing device (e.g., remote computing device 708 or server 710 of FIG. 7). Operation 1008 may include transmitting the BAC and/or notification over a wireless network via a communications interface. Operation 1008 may include displaying the notification and/or BAC via the remote computing device (through a client device communicably coupled to the remote computing device, through a software application, etc.). For example, operation 1008 may include pushing messages to a mobile phone, triggering a text message notification, etc.

At 1010, the space controller (and/or remote computing device or service) operates a controlled device based on a determination that the BAC exceeds a threshold value. Operation 1010 may include operating the controlled device based on the BAC to prevent a user from accessing a space within a building and/or operating the controlled device. For example, operation 1010 may include locking a door to a lab space, manufacturing facility, or another space based on a determination that the BAC of the occupant is above a legal limit. Operation 1010 may additionally include activating remote door locks for a vehicle and/or disabling an ignition system of the vehicle to prevent the occupant from operating the vehicle while intoxicated. Operation 1010 may additionally include disabling a garage door or another vehicle access door to prevent the occupant from moving the vehicle.

In some embodiments, the control operations performed by the space controller (and/or remote computing device) are triggered based on different tiered thresholds. For example, the space controller and/or remote computing device may be configured to prevent a user from performing different actions based on different thresholds. For example, the space controller may prevent the occupant from operating a vehicle based on a determination that the occupant's BAC exceeds a first tiered threshold value (e.g., a legal BAC limit), while still providing a user access to online services such as social media sites and financial services (e.g., online banking, etc.). The remote computing device may be configured to restrict access and/or functionality of these online services based on a determination that the occupant's BAC exceeds a second tiered threshold value that is greater than the first tiered threshold value. The second tiered threshold value may be user specified or may be preprogrammed into the space controller and/or remote computing device based on empirical data. It will be appreciated that the foregoing control schemes are provided for illustrative purposes only. Various alternatives and combinations are possible without departing from the inventive concepts disclosed herein.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A sensor unit, comprising:
  an air quality sensor configured to generate air quality data, the air quality data comprising a value for volatile organic compounds, the sensor unit forming part of a space controller disposed within a building and configured to operate HVAC equipment based on user inputs, the sensor unit configured to:
    determine a first health metric indicative of an air quality within a space in which the sensor unit is located based on the value in a first mode of operation;
    switch from the first mode of operation to a second mode of operation in which the air quality sensor is configured to receive a sample of air from a person's breath over a predefined time interval;
    determine a second health metric indicative of a person's health based on the value in the second mode of operation, wherein the second health metric is associated with the sample of air from the person's breath; and
    generate a notification indicating at least one of the first health metric or the second health metric.

2. The sensor unit of claim 1, wherein the sensor unit is part of a thermostat comprising a temperature sensor configured to measure a temperature, wherein the thermostat further comprises a user interface configured to receive input from a user, wherein the input comprises a temperature preference, and wherein the thermostat is configured to operate a controlled device based on the temperature preference.

3. The sensor unit of claim 1, wherein in the first mode of operation the sensor unit is configured to continuously generate the air quality data while the sensor unit is powered on.

4. The sensor unit of claim 1, wherein in the second mode of operation the sensor unit is configured to generate the air quality data from air flowing over the air quality sensor over another predefined time interval.

5. The sensor unit of claim 4, wherein the second health metric is a blood alcohol content, and wherein the notification is indicative of whether the blood alcohol content exceeds a legal blood alcohol limit.

6. The sensor unit of claim 1, further comprising a proximity sensor, wherein the sensor unit is configured to switch to the second mode based on sensor data from the proximity sensor indicating a person is within a predefined range of the sensor unit.

7. The sensor unit of claim 1, further comprising a user interface configured to display the notification and receive user input, wherein the sensor unit is configured to operate in one of the first mode and the second mode based on the user input.

8. The space controller of claim 1, wherein the sensor unit is further configured to:
  store air quality data from the air quality sensor over another predefined time interval;
  determine a third health metric based on the air quality data over the another predefined time interval; and
  generate a notification indicating the third health metric.

9. A space controller disposed within a building and configured to operate a controlled device, the space controller comprising:
  a user interface configured to present information to a user;
  a sensor unit comprising an air quality sensor configured to generate air quality data, the air quality data comprising a value for volatile organic compounds, the sensor unit forming part of the space controller disposed within the building and configured to operate HVAC equipment comprising the controlled device based on user inputs;
  a processing circuit configured to:
    receive the air quality data from the air quality sensor;
    determine a first health metric indicative of an air quality within a space in which the sensor unit is located based on the value in a first mode of operation;
    switch from the first mode of operation to a second mode of operation in which the air quality sensor is configured to receive a sample of air from a person's breath over a predefined time interval;
    determine a second health metric indicative of a person's health based on the value in the second mode of operation, wherein the second health metric is associated with the sample of air from the person's breath;
    generate a notification indicating at least one of the first health metric or the second health metric; and
    cause the user interface to display the notification.

10. The space controller of claim 9, wherein the space controller is a thermostat comprising a temperature sensor configured to measure a temperature, wherein the user interface is further configured to receive input from the user, wherein the input comprises a temperature preference, and wherein the thermostat is configured to operate the controlled device based on the temperature preference.

11. The space controller of claim 9, wherein in the first mode of operation the processing circuit is configured to continuously receive the air quality data from the air quality sensor while the space controller is powered on.

12. The space controller of claim 9, wherein in the second mode of operation the processing circuit is configured to receive the air quality data from the air quality sensor over a predefined time interval.

13. The space controller of claim 12, wherein the second health metric is a blood alcohol content, and wherein the processing circuit is further configured to operate the controlled device based on a determination that the blood alcohol content exceeds a legal blood alcohol limit.

14. The space controller of claim 9, wherein the processing circuit is configured to operate the controlled device based on the second health metric to prevent the user from at least one of accessing the space within the building or operating the controlled device.

15. The space controller of claim 14, wherein the controlled device is one of a door lock, a security system, a vehicle, or a garage door.

16. The space controller of claim 9, further comprising a memory configured to store air quality data from the air quality sensor over another predefined time interval, wherein the processing circuit is configured to determine a third health metric based on the air quality data over the another predefined time interval, and wherein the processing circuit is configured to cause the user interface to display the third health metric.

17. A method, comprising:
  receiving, from a sensor unit comprising an air quality sensor within a building, air quality data, the air quality data comprising a value for volatile organic compounds, the sensor unit forming part of a space controller disposed within the building and configured to operate HVAC equipment based on user inputs;
  determining a first health metric indicative of an air quality within a space in which the air quality sensor is located based on the value in a first mode of operation;
  switch from the first mode of operation to a second mode of operation in which the air quality sensor is configured to receive a sample of air from a person's breath over a predefined time interval;
  determining a second health metric indicative of a person's health based on the value in the second mode of operation, wherein the second health metric is associated with the sample of air from the person's breath;
  generating a notification indicating at least one of the first health metric or the second health metric; and
  operating a controlled device based on a determination that the at least one of the first health metric or the second health metric exceeds a threshold value.

18. The method of claim 17, wherein the controlled device is operated to prevent a user from at least one of accessing the space within the building or operating the controlled device.

19. The method of claim 17, further comprising receiving, in the second mode of operation, the air quality data from the air quality sensor over another predefined time interval.

20. The method of claim 17, wherein the controlled device is one of a door lock, a security system, a vehicle, or a garage door.

* * * * *